(12) United States Patent
Nishikori

(10) Patent No.: US 12,259,653 B2
(45) Date of Patent: Mar. 25, 2025

(54) RADIATION-SENSITIVE RESIN COMPOSITION, METHOD OF FORMING RESIST PATTERN, AND COMPOUND

(71) Applicant: JSR CORPORATION, Tokyo (JP)

(72) Inventor: Katsuaki Nishikori, Tokyo (JP)

(73) Assignee: JSR CORPORATION, Tokyo (JP)

( * ) Notice: Subject to any disclaimer, the term of this patent is extended or adjusted under 35 U.S.C. 154(b) by 587 days.

(21) Appl. No.: 17/541,422

(22) Filed: Dec. 3, 2021

(65) Prior Publication Data
US 2022/0091508 A1 Mar. 24, 2022

Related U.S. Application Data

(63) Continuation of application No. PCT/JP2020/016474, filed on Apr. 14, 2020.

(30) Foreign Application Priority Data

Jun. 6, 2019 (JP) .................................. 2019-106474

(51) Int. Cl.
| | |
|---|---|
| G03F 7/039 | (2006.01) |
| C07C 51/02 | (2006.01) |
| C07C 55/10 | (2006.01) |
| C07C 55/32 | (2006.01) |
| G03F 7/004 | (2006.01) |
| G03F 7/20 | (2006.01) |
| G03F 7/30 | (2006.01) |
| G03F 7/32 | (2006.01) |
| G03F 7/38 | (2006.01) |
| G03F 7/40 | (2006.01) |

(52) U.S. Cl.
CPC ............ *G03F 7/0392* (2013.01); *C07C 51/02* (2013.01); *C07C 55/10* (2013.01); *C07C 55/32* (2013.01); *G03F 7/0045* (2013.01); *G03F 7/0397* (2013.01); *G03F 7/2004* (2013.01); *G03F 7/322* (2013.01); *G03F 7/38* (2013.01); *G03F 7/40* (2013.01)

(58) Field of Classification Search
CPC ........ G03F 7/0392; G03F 7/0397; G03F 7/30; C07C 51/02; C07C 55/32; C07C 69/63
See application file for complete search history.

(56) References Cited

U.S. PATENT DOCUMENTS

| | | | | |
|---|---|---|---|---|
| 2,438,485 | A * | 3/1948 | Henne ..................... | C07C 51/31 562/541 |
| 5,879,856 | A * | 3/1999 | Thackeray ............ | G03F 7/0045 430/326 |
| 2020/0069674 | A1* | 3/2020 | Vepachedu ........ | A61K 31/4748 |
| 2023/0400766 | A1* | 12/2023 | Fukushima ........... | G03F 7/0045 |

FOREIGN PATENT DOCUMENTS

| | | | |
|---|---|---|---|
| JP | S59-93448 | A | 5/1984 |
| JP | H06-12452 | B2 | 2/1994 |
| JP | H11-212265 | A | 8/1999 |
| JP | 2003005375 | A | 1/2003 |
| JP | 2008083370 | A | 4/2008 |
| JP | 2009134088 | A | 6/2009 |
| JP | 2013216877 | A | 10/2013 |
| JP | 2013231163 | A | 11/2013 |
| WO | WO-2018204713 | A1 * | 11/2018 ............. A61K 31/13 |

OTHER PUBLICATIONS

International Search Report issued Jul. 7, 2020 in PCT/JP2020/016474 (with English translation), 5 pages.
Written Opinion issued Jul. 7, 2020 in PCT/JP2020/016474 (with English translation), 6 pages.
Office Action issued Sep. 26, 2023 in Japanese Patent Application No. 2021-524689 (with machine English translation), 4 pages.
Office Action issued Oct. 11, 2024 in Korean Patent Application No. 10-2021-7039158 (with English translation), 9 pages.
Office Action issued Jan. 7, 2025, in corresponding Japanese Patent Application No. 2023-183077 (with machine English translation), 6 pages.

* cited by examiner

*Primary Examiner* — John S. Chu
(74) *Attorney, Agent, or Firm* — Element IP, PLC

(57) ABSTRACT

A radiation-sensitive resin composition contains: a polymer that includes a structural unit including an acid-labile group; a radiation-sensitive acid generator; and a compound represented by the following formula (1). In the following formula (1), $R^1$ represents a hydrogen atom or a monovalent organic group having 1 to 30 carbon atoms; and $X^{n+}$ represents a radiation-sensitive onium cation having a valency of n, wherein n is an integer of 1 to 3. It is preferable that $R^1$ in the following formula (1) represents an organic group, and that the organic group has a ring structure. It is preferable that $R^1$ in the following formula (1) represents an organic group, and that the organic group is an acid-labile group. $X^{n+}$ in the following formula (1) preferably represents a sulfonium cation, an iodonium cation, or a combination thereof.

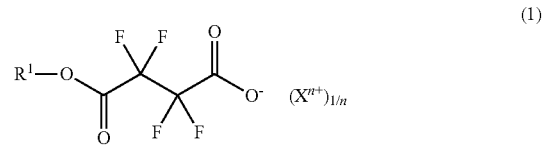

(1)

19 Claims, No Drawings

RADIATION-SENSITIVE RESIN COMPOSITION, METHOD OF FORMING RESIST PATTERN, AND COMPOUND

CROSS-REFERENCE TO RELATED APPLICATIONS

The present application is a continuation application of International Application No. PCT/JP2020/016474, filed Apr. 14, 2020, which claims priority to Japanese Patent Application No. 2019-106474, filed Jun. 6, 2019. The contents of these applications are incorporated herein by reference in their entirety.

BACKGROUND OF THE INVENTION

Field of the Invention

The present invention relates to a radiation-sensitive resin composition, a method of forming a resist pattern, and a compound.

Description of the Related Art

Microfabrication of various types of electronic device structures such as semiconductor devices and liquid crystal devices has been accompanied by a requirement for further microfabrication of resist patterns in lithography processes, and a variety of radiation-sensitive resin compositions have been investigated for this purpose. Such a radiation-sensitive resin composition generates an acid in a light-exposed region upon irradiation with exposure light, e.g., a far ultraviolet ray such as an ArF excimer laser, an extreme ultraviolet ray (EUV), or an electron beam, to cause by a catalytic action of the acid a difference in a rate of dissolution in a developer solution between the light-exposed region and a light-unexposed region, thereby allowing a resist pattern to be formed on a substrate.

There is a requirement for such a radiation-sensitive resin composition to be superior in resolution. To address this requirement, structures of the polymers contained in radiation-sensitive resin compositions have been extensively studied, and it is known that incorporation of a lactone structure such as a butyrolactone structure or a norbornane-lactone structure can serve to enhance the adhesiveness of the resist pattern to the substrate and improve the aforementioned performance (see Japanese Unexamined Patent Application, Publication Nos. H11-212265, 2003-5375 and 2008-83370).

SUMMARY OF THE INVENTION

Along with the further microfabrication of resist patterns, extreme ultraviolet rays (EUV), electron beams, and the like have come to be used as exposure light, thus necessitating an improvement in sensitivity of the radiation-sensitive resin composition. Furthermore, along with the further microfabrication of resist patterns, slight fluctuations in exposure and development conditions have come to exert an increasingly larger effect on configurations and generation of defects of resist patterns. Thus, a radiation-sensitive resin composition with a broad process window (process latitude) which enables absorption of such slight fluctuations in process conditions is also required.

According to one aspect of the invention made for solving the aforementioned problems, a radiation-sensitive resin composition contains: a polymer (may be also referred to as "(A) polymer" or "polymer (A)") having a structural unit including an acid-labile group; a radiation-sensitive acid generator (may be also referred to as "(B) acid generator" or "acid generator (B)"); and a compound (may be also referred to as "(C) compound" or "compound (C)") represented by the following formula (1).

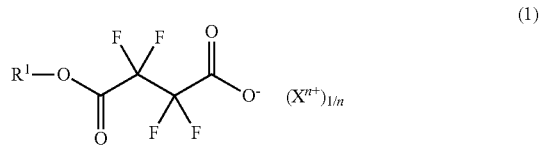

(1)

In the formula (1), $R^1$ represents a hydrogen atom or a monovalent organic group having 1 to 30 carbon atoms. $X^{n+}$ represents a radiation-sensitive onium cation having a valency of n, wherein n is an integer of 1 to 3.

According to an other aspect of the present invention, a method of forming a resist pattern includes applying the radiation-sensitive resin composition of the one aspect of the present invention directly or indirectly on a substrate. A resist film formed by the applying is exposed. The resist film exposed is developed.

Still another aspect, of the present invention made for solving the aforementioned problems is a compound represented by the following formula (1).

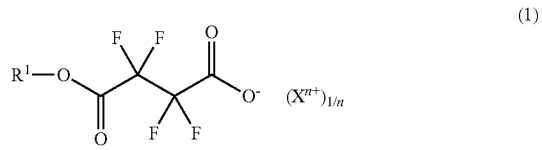

(1)

In the formula (1), $R^1$ represents a hydrogen atom or a monovalent organic group having 1 to 30 carbon atoms. $X^{n+}$ represents a radiation-sensitive onium cation having a valency of n, wherein n is an integer of 1 to 3.

According to one embodiment of the invention, a radiation-sensitive resin composition contains: a polymer (may be also referred to as "(A) polymer" or "polymer (A)") having a structural unit including an acid-labile group; a radiation-sensitive acid generator (may be also referred to as "(B) acid generator" or "acid generator (B)"); and a compound (may be also referred to as "(C) compound" or "compound (C)") represented by the following formula (1):

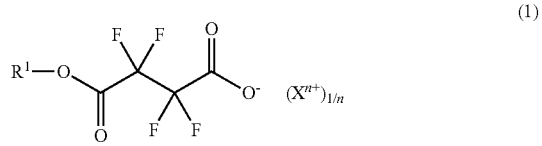

(1)

wherein, in the formula (1), $R^1$ represents a hydrogen atom or a monovalent organic group having 1 to 30 carbon atoms; and $X^{n+}$ represents a radiation-sensitive onium cation having a valency of n, wherein n is an integer of 1 to 3.

According to an other embodiment of the present invention, a method of forming a resist pattern includes: applying the radiation-sensitive resin composition of the one embodiment of the present invention directly or indirectly on a substrate; exposing a resist film formed by the applying; and developing the resist film exposed.

Still another embodiment of the present invention is a compound represented by the following formula (1):

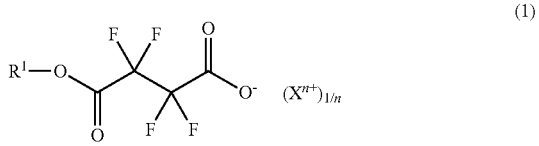

wherein, in the formula (1), R¹ represents a hydrogen atom or a monovalent organic group having 1 to 30 carbon atoms; and $X^{n+}$ represents a radiation-sensitive onium cation having a valency of n, wherein n is an integer of 1 to 3.

The "organic group" as referred to herein means a group that has at least one carbon atom.

The radiation-sensitive resin composition and the method of forming a resist pattern of the embodiments of the present invention enable forming a resist pattern with superior sensitivity and a broad process window. The compound of the still another embodiment of the present invention can be suitably used as a component of the radiation-sensitive resin composition of the one embodiment of the present invention. Therefore, these can be suitably used in manufacturing processes of semiconductor devices, in which further progress of miniaturization is expected in the future.

Radiation-Sensitive Resin Composition

The radiation-sensitive resin composition of the one embodiment of the present invention contains the polymer (A), the acid generator (B), and the compound (C). The radiation-sensitive resin composition typically contains a solvent (may be also referred to as "(D) solvent" or "solvent (D)"), and may also contain, within a range not leading to impairment of the effects of the present invention, other optional component(s).

Due to containing the polymer (A), the acid generator (B), and the compound (C), the radiation-sensitive resin composition is superior in sensitivity, and the process window is broad. Although not necessarily clarified and without wishing to be bound by any theory, the reason for achieving the aforementioned effects by the radiation-sensitive resin composition due to involving such a constitution may be presumed, for example, as in the following. The compound (C) has a —CF₂CF₂— group which is adjacent to a —COO⁻ group. It is considered that a fluorine atom in the —CF₂CF₂— group absorbs exposure light such as EUV, and promotes generation of an acid from the acid generator (B) due to generation of secondary electrons and the like, and it is believed that as a result, the sensitivity of the radiation-sensitive resin composition is improved. Furthermore, it is considered that since the compound (C) has appropriate hydrophobicity, and the —COO⁻ group adjacent to the —CF₂CF₂— group has appropriate basicity, an acid diffusion control property can be effectively demonstrated. It is considered that as a result, a configuration of the resist pattern becomes more favorable, and the process window is expanded.

Hereinafter, each component will be described.

(A) Polymer

The polymer (A) has a structural unit (hereinafter, may be also referred to as "structural unit (I)") including an acid-labile group. The "acid-labile group" as referred to herein means a group that substitutes for a hydrogen atom of a carboxy group, a hydroxy group, or the like, and is dissociable by an action of an acid.

Aside from the structural unit (I), the polymer (A) preferably also has a structural unit (hereinafter, may be also referred to as "structural unit (II)") including a phenolic hydroxyl group, and may also have an other structural unit aside from the structural unit (I) and the structural unit (II). Each structural unit will be described below.

Structural Unit (I)

The structural unit (I) includes the acid-labile group.

Examples of the structural unit (I) include: structural units (hereinafter, may be also referred to as "structural units (I-1A), (I-1B), (I-2A), and (1-2B)") represented by the following formulae (2-1A), (2-1B), (2-2A), and (2-2B); a structural unit (hereinafter, may be also referred to as "structural unit (I-3)") including an acetal structure; and the like.

(2-1A)

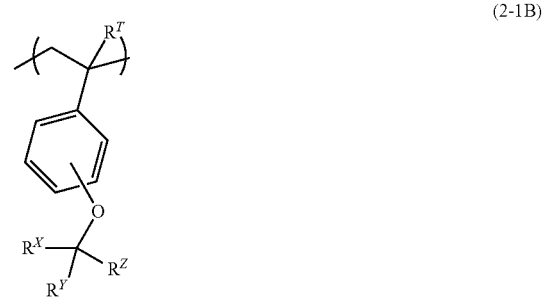

(2-1B)

(2-2A)

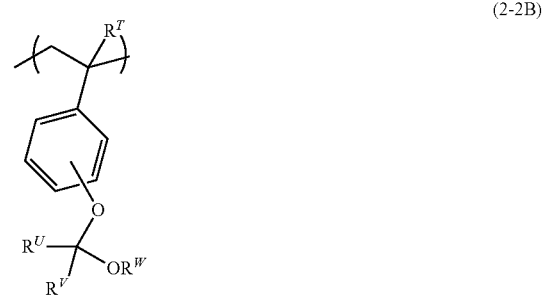

(2-2B)

In the above formula (2-1A), $R^T$ represents a hydrogen atom, a fluorine atom, a methyl group, or a trifluoromethyl group; $R^X$ represents a hydrogen atom or a monovalent hydrocarbon group having 1 to 20 carbon atoms; and $R^Y$ and $R^Z$ each independently represent a monovalent hydrocarbon group having 1 to 20 carbon atoms, or $R^Y$ and $R^Z$ taken together represent an alicyclic structure having 3 to 20 ring atoms together with the carbon atom to which $R^Y$ and $R^Z$ bond.

In the above formula (2-1B), $R^T$ represents a hydrogen atom, a fluorine atom, a methyl group, or a trifluoromethyl group; $R^X$ represents a monovalent hydrocarbon group having 1 to 20 carbon atoms; and $R^Y$ and $R^Z$ each independently represent a monovalent hydrocarbon group having 1 to 20 carbon atoms, or $R^Y$ and $R^Z$ taken together represent an alicyclic structure having 3 to 20 ring atoms together with the carbon atom to which $R^Y$ and $R^Z$ bond.

In the above formula (2-2A), $R^T$ represents a hydrogen atom, a fluorine atom, a methyl group, or a trifluoromethyl group; $R^U$ represents a hydrogen atom or a monovalent hydrocarbon group having 1 to 20 carbon atoms; and $R^V$ and $R^W$ each independently represent a monovalent hydrocarbon group having 1 to 20 carbon atoms, or $R^V$ and $R^W$ taken together represent an aliphatic heterocyclic structure having 4 to 20 ring atoms together with the carbon atom to which $R^U$ bonds and the oxygen atom adjacent to the carbon atom.

In the above formula (2-2B), $R^T$ represents a hydrogen atom, a fluorine atom, a methyl group, or a trifluoromethyl group; $R^U$ represents a hydrogen atom or a monovalent hydrocarbon group having 1 to 20 carbon atoms; and $R^V$ and $R^W$ each independently represent a monovalent hydrocarbon group having 1 to 20 carbon atoms, or $R^V$ and $R^W$ taken together represent an aliphatic heterocyclic structure having 4 to 20 ring atoms together with the carbon atom to which $R^U$ bonds and the oxygen atom adjacent to the carbon atom.

In each of the structural units (I-1A) to (I-2R), —$CR^XR^YR^Z$ or —$CR^UR^V(OR^W)$ bonding to an oxy-oxygen atom derived from the carboxy group or the phenolic hydroxyl group corresponds to the acid-labile group.

In light of copolymerizability of a monomer that gives the structural unit (I), $R^T$ represents preferably a hydrogen atom or a methyl group.

The "hydrocarbon group" as referred to herein may be exemplified by a chain hydrocarbon group, an alicyclic hydrocarbon group, and an aromatic hydrocarbon group. The "hydrocarbon group" may be either a saturated hydrocarbon group or an unsaturated hydrocarbon group. The "chain hydrocarbon group" as referred to herein means a hydrocarbon group not including a cyclic structure but being constituted with only a chain structure, and may be exemplified by both a linear hydrocarbon group and a branched hydrocarbon group. The "alicyclic hydrocarbon group" as referred to herein means a hydrocarbon group that includes, as a ring structure, not an aromatic ring structure but an alicyclic structure alone, and may be exemplified by both a monocyclic alicyclic hydrocarbon group and a polycyclic alicyclic hydrocarbon group. With regard to this, it is not necessary for the alicyclic hydrocarbon group to be constituted with only an alicyclic structure; it may include a chain structure in a part thereof. The "aromatic hydrocarbon group" as referred to herein means a hydrocarbon group that includes an aromatic ring structure as a ring structure. With regard to this, it is not necessary for the aromatic hydrocarbon group to be constituted with only an aromatic ring structure; it may include a chain structure or an alicyclic structure in a part thereof. The number of "ring atoms" as referred to herein means the number of atoms constituting the ring in the alicyclic structure, the aromatic ring structure, the aliphatic heterocyclic structure, or the aromatic heterocyclic structure, and in the case of a polycyclic ring structure, the number of "ring atoms" means the number of atoms constituting the polycyclic ring.

The monovalent hydrocarbon group having 1 to 20 carbon atoms which may be represented by $R^X$, $R^Y$, $R^Z$, $R^U$, $R^V$, or $R^W$ is exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include:

alkyl groups such as a methyl group, an ethyl group, an n-propyl group, and an i-propyl group;

alkenyl groups such as an ethenyl group, a propenyl group, and a butenyl group; alkynyl groups such as an ethynyl group, a propynyl group, and a butynyl group; and the like.

Examples of the monovalent alicyclic hydrocarbon group having 3 to 20 carbon atoms include:

saturated monocyclic alicyclic hydrocarbon groups such as a cyclopentyl group and a cyclohexyl group;

unsaturated monocyclic alicyclic hydrocarbon groups such as a cyclopentenyl group and a cyclohexenyl group;

saturated polycyclic alicyclic hydrocarbon groups such as a norbornyl group, an adamantyl group, and a tricyclodecyl group;

unsaturated polycyclic alicyclic hydrocarbon groups such as a norbornenyl group and a tricyclodecenyl group; and the like.

Examples of the monovalent aromatic hydrocarbon group having 6 to 20 carbon atoms include:

aryl groups such as a phenyl group, a tolyl group, a xylyl group, a naphthyl group, and an anthryl group;

aralkyl groups such as a benzyl group, a phenethyl group, a naphthylmethyl group, and an anthrylmethyl group; and the like.

Examples of the alicyclic structure having 3 to 20 carbon atoms which may be represented by $R^Y$ and $R^Z$ taken together, together with the carbon atom, include:

monocyclic alicyclic structures such as a cyclopropane structure, a cyclobutane structure, a cyclopentane structure, a cyclohexane structure, a cyclopentene structure, and a cyclohexene structure;

polycyclic alicyclic structures such as a norbornane structure and an adamantane structure; and the like.

Examples of the aliphatic heterocyclic structure having 4 to 20 carbon atoms which may be represented by $R^V$ and $R^W$ taken together, together with the carbon atom and the oxygen atom, include:

monocyclic aliphatic heterocyclic structures such as an oxacyclobutane structure, an oxacyclopentane structure, an oxacyclohexane structure, an oxacyclopentene structure, and an oxacyclohexene structure;

polycyclic aliphatic heterocyclic structures such as an oxanorbornane structure and an oxaadamantane structure; and the like.

The structural unit (I-1A) is preferably one of structural units (hereinafter, may be also referred to as "structural units (I-1A-1) to (I-1A-6)") represented by the following formulae (2-1A-1) to (2-1A-6).

(2-1A-1)
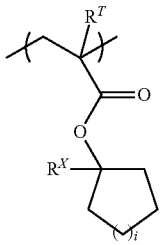

(2-1A-2)
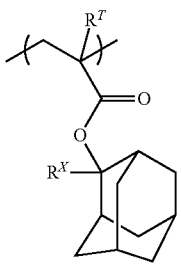

(2-1A-3)
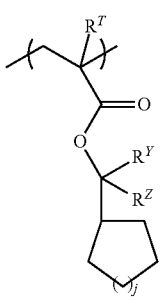

(2-1A-4)
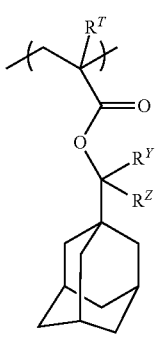

(2-1A-5)
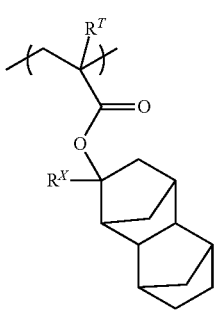

(2-1A-6)
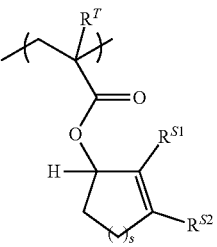

In each of the above formulae (2-1A-1) to (2-1A-5), $R^1$, $R^X$, $R^Y$, and $R^Z$ are as defined in the above formula (2-1A); and i and j are each independently an integer of 1 to 4.

In the above formula (2-1A-6), $R^T$ is as defined in the above formula (2-1A); s is an integer of 1 to 4; and $R^{S1}$ and $R^{S2}$ each independently represent a hydrogen atom or a monovalent hydrocarbon group having 1 to 10 carbon atoms.

$R^X$ represents preferably an alkyl group having 1 to 4 carbon atoms or an aryl group having 6 to 10 carbon atoms, and more preferably a methyl group, an ethyl group, an i-propyl group, a t-butyl group, or a phenyl group.

$R^{S1}$ and $R^{S2}$ each independently represent preferably a hydrogen atom or a methyl group.

i and j are each preferably 1 or 2.

s is preferably 2.

The structural unit (I) is preferably the structural unit (I-1A), and more preferably the structural unit (I-1A-1) or the structural unit (I-1A-6).

Structural Unit (I-3)

The structural unit (I-3) includes an acetal structure. Examples of a group including the acetal structure include a group (hereinafter, may be also referred to as "group (X)") represented by the following formula (3). The group (X) generates *—$R^1$—OH, $R^J R^K C$=O, and $R^L$OH through degradation by an action of an acid. In the group (X), —$CR^J R^K$ ($OR^L$) corresponds to the acid-labile group.

(3)
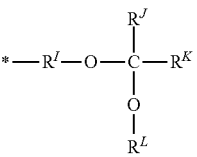

In the above formula (3), $R^1$ represents a single bond or a divalent hydrocarbon group having 1 to 20 carbon atoms, $R^J$ and $R^K$ each independently represent a hydrogen atom or a monovalent hydrocarbon group having 1 to 20 carbon atoms, and $R^L$ represents a monovalent hydrocarbon group having 1 to 20 carbon atoms, or at least two of $R^I$, $R^J$, $R^K$, and $R^L$ taken together represent a ring structure having 3 to 20 ring atoms, together with the carbon atom or the atom chain to which the at least two of $R^I$, $R^J$, $R^K$, and $R^L$ bond; and * denotes a binding site to a part other than the group (X) in the structural unit (I-3).

Examples of the divalent hydrocarbon group having 1 to 20 carbon atoms which may be represented by $R^I$ include a group obtained by removing one hydrogen atom from the monovalent hydrocarbon group having 1 to 20 carbon atoms exemplified as each of $R^X$, $R^Y$, and $R^Z$, and the like.

$R^I$ represents preferably a single bond or a divalent chain hydrocarbon group having 1 to 20 carbon atoms, more preferably a divalent chain hydrocarbon group having 1 to 20 carbon atoms, still more preferably an alkanediyl group having 1 to 10 carbon atoms, and particularly preferably a methanediyl group.

Examples of the monovalent hydrocarbon group having 1 to 20 carbon atoms which may be represented by $R^J$, $R^K$, or $R^L$ include groups similar to the groups exemplified as the monovalent hydrocarbon group having 1 to 20 carbon atoms which may be represented by $R^X$, $R^Y$, or $R^Z$; and the like.

$R^J$ and $R^K$ each independently represent preferably a hydrogen atom or a chain hydrocarbon group, more preferably a hydrogen atom or an alkyl group, and still more preferably a hydrogen atom or a methyl group. $R^Z$ represents preferably a chain hydrocarbon group, more preferably an alkyl group, and particularly preferably a methyl group.

$R^I$ represents preferably a single bond or a chain hydrocarbon group, more preferably a chain hydrocarbon group, still more preferably an alkanediyl group, and particularly preferably a methanediyl group.

Examples of the ring structure having 5 to 20 ring atoms which may be represented by $R^I$ and $R^L$ taken together, together with the atom chain, include 1,3-dioxacycloalkane structures such as a 1,3-dioxacyclopentane structure, and the like.

Examples of the ring structure having 3 to 20 ring atoms which may be represented by $R^J$ and $R^K$ taken together, together with the carbon atom, include cycloalkane structures such as a cyclopentane structure and a cyclohexane structure, and the like.

Examples of the group (X) include a 2,2-dimethyl-1,3-dioxacyclopentan-4-yl group, and the like.

The lower limit of a proportion of the structural unit (I) contained with respect to total structural units constituting the polymer (A) is preferably 20 mol %, more preferably 40 mol %, and still more preferably 50 mol %. The upper limit of the proportion is preferably 90 mol %, more preferably 80 mol %, and still more preferably 70 mol %. When the proportion of the structural unit (I) falls within the above range, the sensitivity and the process window can be further improved.

Structural Unit (II)

The structural unit (II) includes the phenolic hydroxyl group. The "phenolic hydroxyl group" as referred to herein is not limited to a hydroxy group directly bonding to a benzene ring, and means any hydroxy group directly bonding to an aromatic ring in general. When the polymer (A) contains the structural unit (II), hydrophilicity of the resist film can be increased and solubility in a developer solution can be appropriately adjusted, and as a result, the process window can be further expanded. Furthermore, in a case of KrF exposure, EUV exposure, or electron beam exposure, the sensitivity can be further improved.

Examples of the structural unit (II) include structural units represented by the following formula (P), and the like,

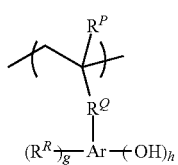

(P)

In the above formula (P), $R^P$ represents a hydrogen atom, a fluorine atom, a methyl group, or a trifluoromethyl group; $R^Q$ represents a single bond, —O—, —COO—, or —CONH—; Ar represents a group obtained by removing (g+h+1) hydrogen atoms on an aromatic ring from an arene having 6 to 20 ring atoms; g is an integer of 0 to 10, wherein in a case in which g is 1, $R^R$ represents a halogen atom or a monovalent organic group having 1 to 20 carbon atoms, in a case in which g is no less than 2, a plurality of $R^R$s are identical or different from each other and each $R^R$ represents a halogen atom or a monovalent organic group having 1 to 20 carbon atoms, or at least two of the plurality of $R^R$S taken together represent a ring structure having 4 to 20 ring atoms together with the carbon chain to which the at least two $R^R$s bond; and h is an integer of 1 to 11, wherein a sum of g and h is no greater than 11.

In light of copolymerizability of a monomer that gives the structural unit (II), $R^P$ represents preferably a hydrogen atom or a methyl group, and more preferably a hydrogen atom.

$R^Q$ represents preferably a single bond or —COO—, and more preferably a single bond.

The monovalent organic group having 1 to 20 carbon atoms which may be represented by $R^R$ is exemplified by: a monovalent hydrocarbon group having 1 to 20 carbon atoms; a monovalent group (α) that includes a divalent hetero atom-containing group between two adjacent carbon atoms of the monovalent hydrocarbon group having 1 to 20 carbon atoms; a monovalent group (β) obtained by substituting with a monovalent hetero atom-containing group, a part or all of hydrogen atoms included in the monovalent hydrocarbon group having 1 to 20 carbon atoms or the monovalent group (α); a monovalent group (γ) obtained by combining a divalent hetero atom-containing group with the monovalent hydrocarbon group having 1 to 20 carbon atoms, the monovalent group (α), or the monovalent group (β); and the like.

Examples of the monovalent hydrocarbon group having 1 to 20 carbon atoms include groups similar to the monovalent hydrocarbon groups having 1 to 20 carbon atoms exemplified as $R^X$ to $R^W$ in the above formulae (2-1A) to (2-2B), and the like.

The hetero atom constituting the monovalent hetero atom-containing group or the divalent hetero atom-containing group is exemplified by an oxygen atom, a nitrogen atom, a sulfur atom, a phosphorus atom, a silicon atom, a halogen atom, and the like. Examples of the halogen atom include a fluorine atom, a chlorine atom, a bromine atom, an iodine atom, and the like.

Examples of the divalent hetero atom-containing group include —O—, —CO—, —S—, —CS—, —NR'—, a combination of two or more of these, and the like, wherein R' represents a hydrogen atom or a monovalent hydrocarbon group. Of these, —CO— is preferred.

Examples of the monovalent hetero atom-containing group include a halogen atom, a hydroxy group, a carboxy group, a cyano group, an amino group, a sulfanyl group, and the like.

Examples of the arene having 6 to 20 ring atoms that gives Ar include benzene, naphthalene, anthracene, phenanthrene, tetracene, pyrene, and the like. Of these, benzene or naphthalene is preferred, and benzene is more preferred.

$R^R$ represents preferably a hydrocarbon group, and more preferably an alkyl group.

Examples of the ring structure having 4 to 20 ring atoms which may be represented by the at least two of the plurality of $R^R$s taken together, together with the carbon chain, include alicyclic structures such as a cyclohexane structure and a cyclohexene structure, and the like.

g is preferably 0 to 2, more preferably 0 or 1, and still more preferably 0.

h is preferably 1 to 3, more preferably 1 or 2, and still more preferably 1.

Examples of the structural unit (II) include structural units (hereinafter, may be also referred to as "structural units (II-1) to (II-14)") represented by the following formulae (P-1) to (P-14), and the like.

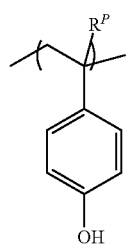
(P-1)

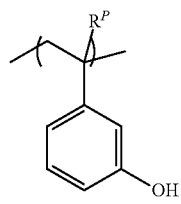
(P-2)

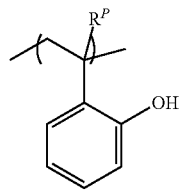
(P-3)

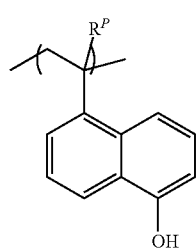
(P-4)

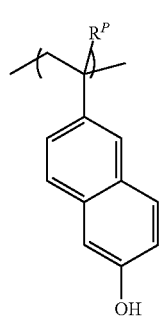
(P-5)

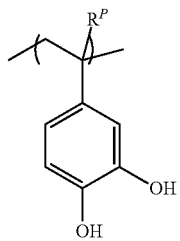
(P-6)

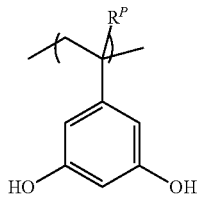
(P-7)

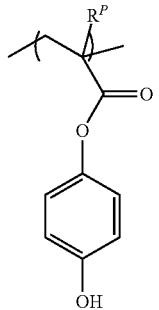
(P-8)

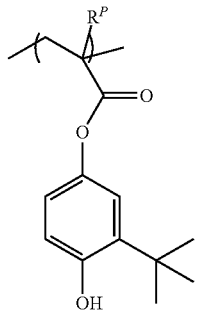
(P-9)

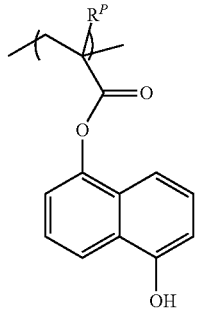
(P-10)

-continued (P-11)
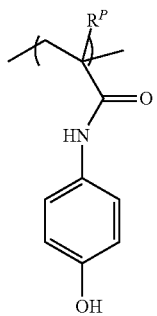

(P-12)
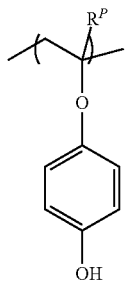

(P-13)
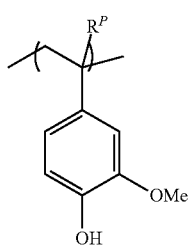

(P-14)
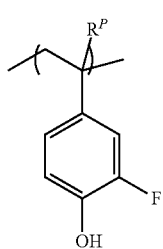

In the above formulae (P-1) to (P-14), $R^P$ is as defined in the above formula (P).

Of these, the structural unit (II-1) or (II-2) is preferred.

In a case in which the polymer (A) has the structural unit (II), the lower limit of a proportion of the structural unit (II) contained with respect to total structural units constituting the polymer (A) is preferably 10 mol %, more preferably 20 mol %, and still more preferably 25 mol %. The upper limit of the proportion is preferably 80 mol %, more preferably 60 mol %, and still more preferably 50 mol %. When the proportion of the structural unit (II) falls within the above range, the sensitivity and the process window of the radiation-sensitive resin composition can be further improved.

The structural unit (II) may be formed by, e.g., hydrolyzing in the presence of a base such as triethylamine, a polymer obtained by using a monomer such as, e.g., an acyloxystyrene such as acetoxystyrene.

Other Structural Unit

The other structural unit is exemplified by: a structural unit including an alcoholic hydroxyl group; a structural unit including a lactone structure, a cyclic carbonate structure, a sultone structure, or a combination thereof; a structural unit including a carboxy group, a cyano group, a nitro group, a sulfonamide group, or a combination thereof; a structural unit including an acid-nonlabile hydrocarbon group; and the like.

Examples of the structural unit including an alcoholic hydroxyl group include structural units represented by the following formulae, and the like.

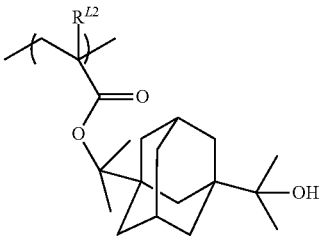

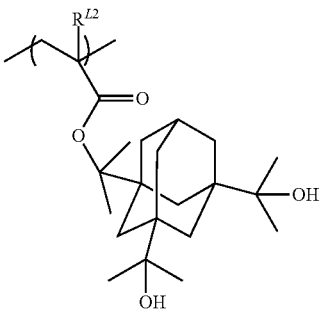

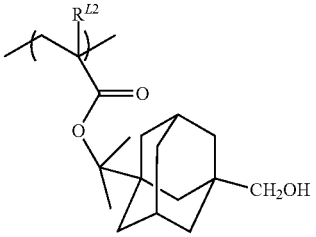

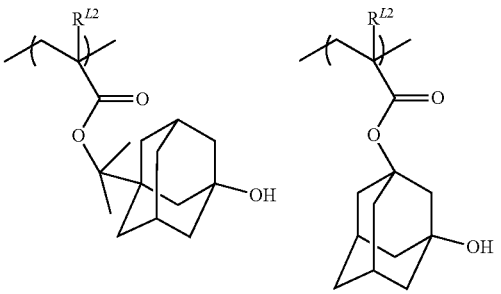

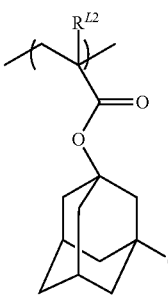

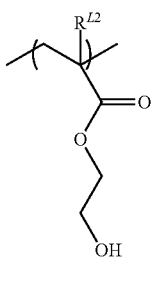

-continued

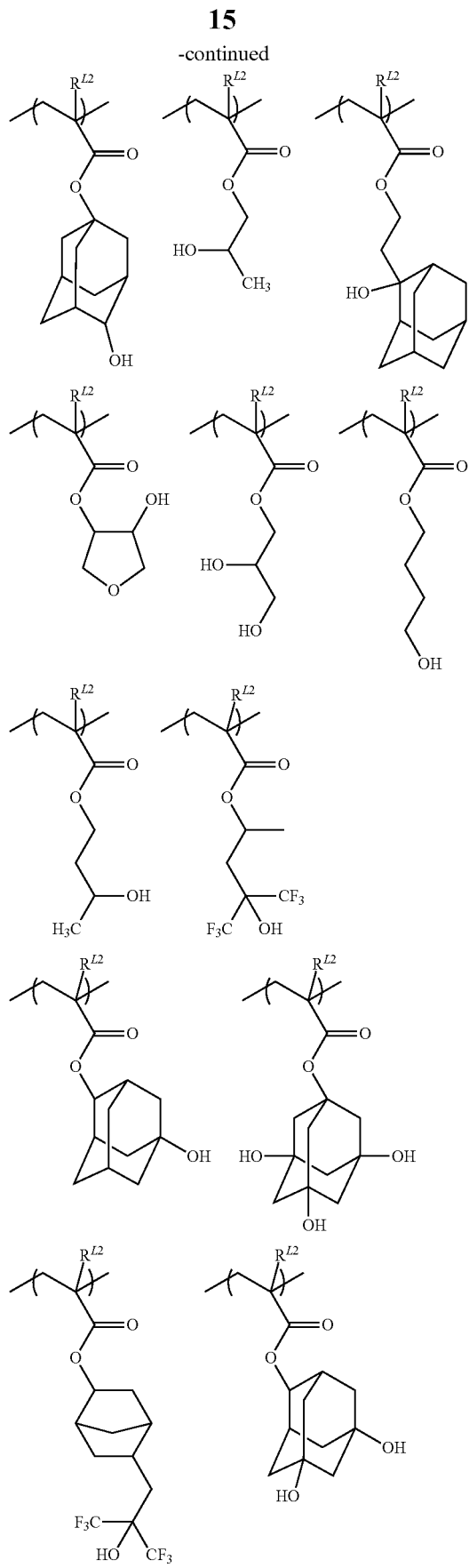
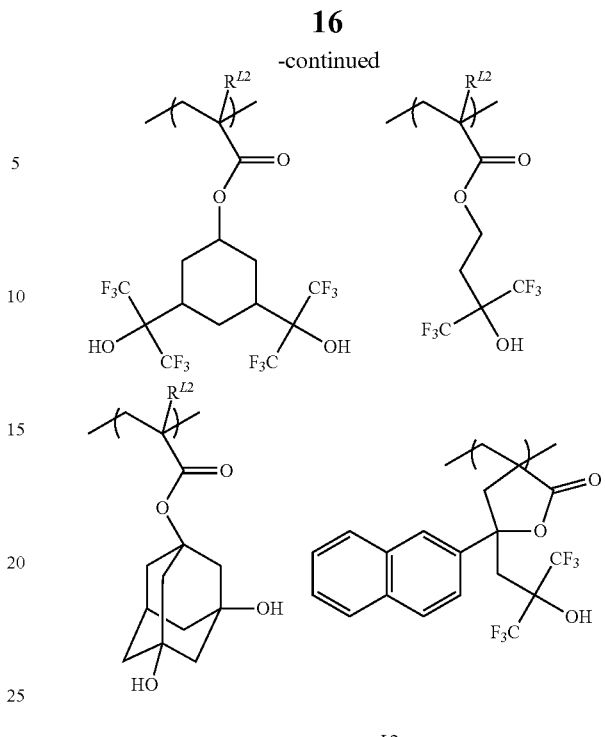

In each of the above formulae, $R^{L2}$ represents a hydrogen atom, a fluorine atom, a methyl group, or a trifluoromethyl group.

In the case in which the polymer (A) has the other structural unit, the upper limit of a proportion of the other structural unit contained with respect to total structural units constituting the polymer (A) is preferably 30 mol %, and more preferably 15 mol %.

The lower limit of a proportion of the polymer (A) with respect to total components other than the solvent (D) in the radiation-sensitive resin composition is preferably 50% by mass, more preferably 70% by mass, and still more preferably 80% by mass. The upper limit of the proportion is preferably 99 mol %, and more preferably 95 mol %.

The lower limit of a proportion of the polymer (A) in the radiation-sensitive resin composition is preferably 0.1% by mass, more preferably 0.5% by mass, and still more preferably 1% by mass. The upper limit of the proportion is preferably 50% by mass, more preferably 30% by mass, and still more preferably 10% by mass. One, or two or more types of the polymer (A) may be contained.

Synthesis Method of Polymer (A)

The polymer (A) can be synthesized by, for example, polymerizing a monomer that gives each structural unit by using a radical polymerization initiator or the like in a solvent.

The lower limit of a polystyrene equivalent weight average molecular weight (Mw) of the polymer (A) as determined by gel permeation chromatography (GPC) is preferably 1,000, more preferably 3,000, still more preferably 4,000, and particularly preferably 5,000. The upper limit of the Mw is preferably 50,000, more preferably 30,000, still more preferably 20,000, and particularly preferably 10,000. When the Mw of the polymer (A) falls within the above range, the coating characteristics of the radiation-sensitive resin composition can be improved, and as a result, the sensitivity and the process window can be further improved.

The upper limit of a ratio (Mw/Mn) of the Mw with respect to a polystyrene equivalent number average molecular weight (Mn) of the polymer (A) as determined by GPC is preferably 5, more preferably 3, still more preferably 2, and particularly preferably 1.6. The lower limit of the ratio is typically 1, and preferably 1.1.

The Mw and the Mn of the polymer as referred to herein are values determined using gel permeation chromatography (GPC) under the following conditions.

GPC columns: "G2000 HXL"×2, "G3000 HXL"×1, and "G4G00 HXL"×1, each available from Tosoh Corporation;

column temperature: 40° C.

elution solvent: tetrahydrofuran (FUJIFILM Wake Pure Chemical Corporation)

flow rate: 1.0 mL/min sample concentration: 1.0% by mass amount of injected sample: 100 uL detector: differential refractometer standard substance: mono-dispersed polystyrene (B) Acid Generator The acid generator (B) is a substance that generates an acid upon exposure. The acid thus generated allows the acid-labile group included in the polymer (A) or the like to be dissociated, thereby generating a carboxy group, a hydroxy group, etc., whereby solubility of the polymer (A) in the developer solution changes and thus formation of a resist pattern from the radiation-sensitive resin composition is enabled. The acid generator (B) may be contained in the radiation-sensitive resin composition either in the form of a low-molecular-weight compound (hereinafter, may be also referred to as "(B) acid generating agent" or "acid generating agent (B)") or in the form of an acid generator incorporated as a part of the polymer, or may be in both of these forms.

Examples of the acid generated from the acid generator (B) include sulfonic acid, imidic acid, and the like.

The acid generating agent (B) is exemplified by an onium salt compound, an N-sulfonyloxyimide compound, a sulfonimide compound, a halogen-containing compound, a diazoketone compound, and the like.

Examples of the onium salt compound include sulfonium salts, tetrahydrothiophenium salts, iodonium salts, phosphonium salts, diazonium salts, pyridinium salts, and the like.

Specific examples of the acid generating agent (B) include compounds disclosed in paragraphs [0080] to [0113] of Japanese Unexamined Patent Application, Publication No. 2009-134088, and the like.

Examples of the acid generating agent (B) include a compound represented by the following formula (4), and the like.

$$A^- T^+ \quad (4)$$

In the above formula (4), $A^-$ represents a monovalent sulfonic acid anion or a monovalent imidic acid anion; and $T^+$ represents a monovalent radiation-sensitive onium cation.

The acid generating agent (B) that generates sulfonic acid upon exposure is exemplified by a compound (hereinafter, may be also referred to as "compound (4-1)") represented by the following formula (4-1), and the like. It is considered that when the acid generating agent (B) has the following structure, a diffusion length of the acid generated upon the exposure in the resist film will be more appropriately shortened through, e.g., an interaction with the polymer (A), and that as a result, the process window can be further expanded.

$$R^{p1}\!-\!\!\left(\!R^{p2}\!\right)_{\!n^{p1}}\!\!\left(\!\!\begin{array}{c}R^{p3}\\|\\C\\|\\R^{p4}\end{array}\!\!\right)_{\!n^{p2}}\!\!\left(\!\!\begin{array}{c}R^{p5}\\|\\C\\|\\R^{p6}\end{array}\!\!\right)_{\!n^{p3}}\!\!SO_3^- \;\; T^+ \quad (4\text{-}1)$$

In the above formula (4-1), $R^{p1}$ represents a monovalent group including a ring structure having 5 or more ring atoms; $R^{p2}$ represents a divalent linking group; $R^{p3}$ and $R^{p4}$ each independently represent a hydrogen atom, a fluorine atom, a monovalent hydrocarbon group having 1 to 20 carbon atoms, or a monovalent fluorinated hydrocarbon group having 1 to 20 carbon atoms; $R^{p5}$ and $R^{p6}$ each independently represent a fluorine atom or a monovalent fluorinated hydrocarbon group having 1 to 20 carbon atoms; $n^{p1}$ is an integer of 0 to 10, $n^{p2}$ is an integer of 0 to 10, and $n^{p3}$ is an integer of 0 to 10, wherein a sum of $n^{p1}$, $n^{p2}$, and $n^{p3}$ is no less than 10 and no greater than 30, in a case in which $n^{p1}$ is no less than 2, a plurality of $R^{p2}$s are identical or different from each other, in a case in which $n^{p2}$ is no less than 2, a plurality of $R^{p3}$s are identical or different from each other and a plurality of $R^{p4}$s are identical or different from each other, and in a case in which $n^{p3}$ is no less than 2, a plurality of $R^{p5}$s are identical or different from each other, and a plurality of $R^{p6}$s are identical or different from each other; and $T^+$ represents a monovalent radiation-sensitive onium cation.

The monovalent group including the ring structure having 5 or more ring atoms which is represented by $R^{p1}$ is exemplified by a monovalent group including an alicyclic structure having 5 or more ring atoms, a monovalent group including an aliphatic heterocyclic structure having 5 or more ring atoms, a monovalent group including an aromatic ring structure having 5 or more ring atoms, a monovalent group including an aromatic heterocyclic structure having 5 or more ring atoms, and the like.

Examples of the alicyclic structure having 5 or more ring atoms include:
monocyclic saturated alicyclic structures such as a cyclopentane structure, a cyclohexane structure, a cycloheptane structure, a cyclooctane structure, a cyclononane structure, a cyclodecane structure, and a cyclododecane structure;
monocyclic unsaturated alicyclic structures such as a cyclopentene structure, a cyclohexene structure, a cycloheptene structure, a cyclooctene structure, and a cyclodecene structure;
polycyclic saturated alicyclic structures such as a norbornane structure, an adamantane structure, a tricyclodecane structure, and a tetracyclododecane structure;
polycyclic unsaturated alicyclic structures such as a norbornene structure and a tricyclodecene structure; and the like.

Examples of the aliphatic heterocyclic structure having 5 or more ring atoms include:
lactone structures such as a hexanolactone structure and a norbornanelactone structure;
sultone structures such as a hexanosultone structure and a norbornanesultone structure:
oxygen atom-containing heterocyclic structures such as an oxacycloheptane structure and an oxanorbornane structure;
nitrogen atom-containing heterocyclic structures such as an azacyclohexane structure and a diazabicyclooctane structure;

sulfur atom-containing heterocyclic structures such as a thiacyclohexane structure and a thianorbornane structure; and the like.

Examples of the aromatic ring structure having 5 or more ring atoms include a benzene structure, a naphthalene structure, a phenanthrene structure, an anthracene structure, and the like.

Examples of the aromatic heterocyclic structure having 5 or more ring atom s include:
oxygen atom-containing heterocyclic structures such as a furan structure, a pyran structure, a benzofuran structure, and a benzopyran structure;
nitrogen atom-containing heterocyclic structures such as a pyridine structure, a pyrimidine structure, and an indole structure; and the like.

The lower limit of the number of ring atoms included in the ring structure of $R^{p1}$ is preferably 6, more preferably 8, still more preferably 9, and particularly preferably 10. The upper limit of the number of ring atoms is preferably 15, more preferably 14, still more preferably 13, and particularly preferably 12. When the number of ring atoms falls within the above range, the diffusion length of the acid can be more appropriately shortened, and as a result, the process window can be further expanded.

A part or all of hydrogen atoms included in the ring structure of $R^{p1}$ may be substituted with a substituent. Examples of the substituent include halogen atoms such as a fluorine atom, a chlorine atom, a bromine atom, and an iodine atom; a hydroxy group; a carboxy group; a cyano group; a nitro group; an alkoxy group; an alkoxycarbonyl group; an alkoxycarbonyloxy group; an acyl group; an acyloxy group; and the like. Of these, a hydroxy group is preferred.

$R^{p1}$ represents preferably a monovalent group including an alicyclic structure having or more ring atoms, or a monovalent group including an aromatic ring structure having 6 or more ring atoms.

Examples of the divalent linking group which may be represented by $R^{p2}$ include a carbonyl group, an ether group, a carbonyloxy group, a sulfide group, a thiocarbonyl group, a sulfonyl group, a divalent hydrocarbon group, and the like. Of these, the carbonyloxy group, the sulfonyl group, an alkanediyl group, or a saturated divalent alicyclic hydrocarbon group is preferred; the carbonyloxy group or the saturated divalent alicyclic hydrocarbon group is more preferred; the carbonyloxy group or a norbornanediyl group is still more preferred; and the carbonyloxy group is particularly preferred.

The monovalent hydrocarbon group having 1 to 20 carbon atoms which may be represented by $R^{p3}$ or $R^{p4}$ is exemplified by an alkyl group having 1 to 20 carbon atoms, and the like. The monovalent fluorinated hydrocarbon group having 1 to 20 carbon atoms which may be represented by $R^{p3}$ or $R^{p4}$ is exemplified by a fluorinated alkyl group having 1 to 20 carbon atoms, and the like. $R^{p3}$ and $R^{p4}$ each independently represent preferably a hydrogen atom, a fluorine atom, or a fluorinated alkyl group; more preferably a fluorine atom or a perfluoroalkyl group; and still more preferably a fluorine atom or a trifluoromethyl group.

The monovalent fluorinated hydrocarbon group having 1 to 20 carbon atoms which may be represented by $R^{p5}$ or $R^{p6}$ is exemplified by a fluorinated alkyl group having 1 to 20 carbon atoms, and the like. $R^{p5}$ and $R^{p6}$ each independently represent preferably a fluorine atom or a fluorinated alkyl group, more preferably a fluorine atom or a perfluoroalkyl group, still more preferably a fluorine atom or a trifluoromethyl group, and particularly preferably a fluorine atom.

$n^{p1}$ is preferably 0 to 5, more preferably 0 to 3, still more preferably 0 to 2, and particularly preferably 0 or 1.

$np^2$ is preferably 0 to 5, more preferably 0 to 2, still more preferably 0 or 1, and particularly preferably 0.

The lower limit of $n^{p3}$ is preferably 1, and more preferably 2. When $n^{p3}$ is no less than 1, strength of the acid generated from the compound (4-1) can be increased, and as a result, the process window can be further expanded. The upper limit of $n^{p3}$ is preferably 8, more preferably 6, and still more preferably 4.

The lower limit of the sum of $n^{p1}$, $n^{p2}$, and $n^{p3}$ is preferably 2, and more preferably 4. The upper limit of the sum of $n^{p1}$, $n^{p2}$, and $n^{p3}$ is preferably 20, and more preferably 10.

The monovalent radiation-sensitive onium cation represented by $T^+$ is exemplified by a cation (hereinafter, may be also referred to as "cation (T-1)") represented by the following formula (T-1), a cation (hereinafter, may be also referred to as "cation (T-2)") represented by the following formula (T-2), a cation (hereinafter, may be also referred to as "cation T-3") represented by the following formula (T-3), and the like.

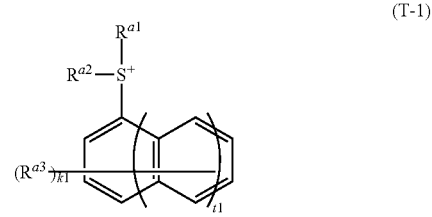

(T-1)

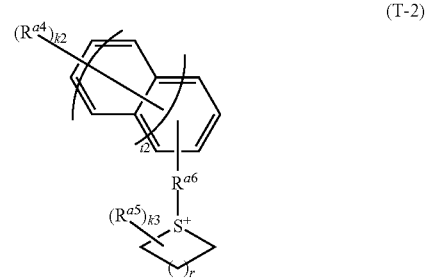

(T-2)

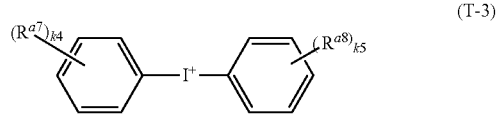

(T-3)

In the above formula (T-1), $R^{a1}$ and $R^{a2}$ each independently represent a monovalent organic group having 1 to 20 carbon atoms; k1 is an integer of 0 to 5, wherein in a case in which k1 is 1, $R^{a3}$ represents a halogen atom, a hydroxy group, a nitro group, or a monovalent organic group having 1 to 20 carbon atoms, and in a case in which k1 is 2 to 5, a plurality of $R^{a3}$s are identical or different from each other, and each $R^{a3}$ represents a halogen atom, a hydroxy group, a nitro group, or a monovalent organic group having 1 to 20 carbon atoms, or the plurality of $R^{a3}$s taken together represent a ring structure having 4 to 20 ring atoms together with the carbon chain to which the plurality of $R^a$, s bond; and t1 is an integer of 0 to 3.

Examples of the monovalent organic group having 1 to 20 carbon atoms which may be represented by $R^{a1}$, $R^{a2}$, or $R^{a3}$ include groups similar to the monovalent organic groups having 1 to 20 carbon atoms exemplified as $R^R$ in the above formula (P), and the like.

$R^{a1}$ and $R^{a2}$ each independently represent preferably a monovalent unsubstituted hydrocarbon group having 1 to 20 carbon atoms or a hydrocarbon group obtained therefrom by substituting a hydrogen atom included therein with a substituent, more preferably a monovalent unsubstituted aromatic hydrocarbon group having 6 to 18 carbon atoms or an aromatic hydrocarbon group obtained therefrom by substituting a hydrogen atom included therein with a substituent, still more preferably a substituted or unsubstituted phenyl group, and particularly preferably an unsubstituted phenyl group.

The substituent which may substitute for the hydrogen atom included in the monovalent hydrocarbon group having 1 to 20 carbon atoms which may be represented by $R^{a1}$ or $R^{a2}$ is preferably —$OSO_2$—$R^k$, —$SO_2$—$R^k$, —$OR^k$, —CO-$OR^k$, —O—CO—$R^k$, —O—$R^{kk}$—$COOR^k$, —$R^{kk}$—CO—$R^k$, —S—$R^k$, or a substituted or unsubstituted monovalent hydrocarbon group having 1 to 20 carbon atoms, wherein $R^k$ represents a monovalent hydrocarbon group having 1 to 10 carbon atoms; and $R^{kk}$ represents a single bond or a divalent hydrocarbon group having 1 to 10 carbon atoms.

$R^{a3}$ represents preferably —$OSO_2$—$R^k$, —$SO_2$—$R^k$, —$OR^k$, —$COOR^k$, —O—CO—$R^k$, —O—$R^{kk}$—$COOR^k$, —$R^{kk}$—CO—$R^k$, —S—$R^k$, or a substituted or unsubstituted monovalent hydrocarbon group having 1 to 20 carbon atoms, wherein $R^k$ represents a monovalent hydrocarbon group having 1 to 10 carbon atoms; and $R^{kk}$ represents a single bond or a divalent hydrocarbon group having 1 to 10 carbon atoms.

In the above formula (T-2), k2 is an integer of 0 to 7, wherein in a case in which k2 is 1, $R^{a4}$ represents a halogen atom, a hydroxy group, a nitro group, or a monovalent organic group having 1 to 20 carbon atoms, and in a case in which k2 is 2 to 7, a plurality of $R^{a4}$s are identical or different from each other, and each $R^{a4}$ represents a halogen atom, a hydroxy group, a nitro group, or a monovalent organic group having 1 to 20 carbon atoms, or the plurality of $R^{a4}$s taken together represent a ring structure having 4 to 20 ring atoms together with the carbon chain to which the plurality of $R^{a4}$s bond; k3 is an integer of 0 to 6, wherein in a case in which k3 is 1, $R^{a5}$ represents a halogen atom, a hydroxy group, a nitro group, or a monovalent organic group having 1 to 20 carbon atoms, and in a case in which k3 is 2 to 6, a plurality of $R^{a5}$s are identical or different from each other, and each $R^{a3}$ represents a halogen atom, a hydroxy group, a nitro group, or a monovalent organic group having 1 to 20 carbon atoms, or the plurality of $R^{a5}$s taken together represent a ring structure having 3 to 20 ring atoms together with the carbon atom or the carbon chain to which the plurality of $R^{a5}$s bond; r is an integer of 0 to 3; $R^{a6}$ represents a single bond or a divalent organic group having 1 to 20 carbon atoms; and t2 is an integer of 0 to 2.

$R^{a4}$ and $R^{a5}$ each independently represent preferably —$OR^k$, —$COOR^k$, —O—CO—$R^k$, —O—$R^{kk}$—$COOR^k$, —$R^{kk}$—CO—$R^k$, or a substituted or unsubstituted monovalent hydrocarbon group having 1 to 20 carbon atoms, wherein $R^k$ represents a monovalent hydrocarbon group having 1 to 10 carbon atoms; and $R^{kk}$ represents a single bond or a divalent hydrocarbon group having 1 to 10 carbon atoms.

In the above formula (T-3), k4 is an integer of 0 to 5, wherein in a case in which k4 is 1, $R^{a7}$ represents a halogen atom, a hydroxy group, a nitro group, or a monovalent organic group having 1 to 20 carbon atoms, and in a case in which k4 is 2 to 5, a plurality of $R^{a7}$s are identical or different from each other, and each $R^{a7}$ represents a halogen atom, a hydroxy group, a nitro group, or a monovalent organic group having 1 to 20 carbon atoms, or the plurality of $R^{a7}$s taken together represent a ring structure having 4 to 20 ring atoms together with the carbon chain to which the plurality of $R^{a7}$s bond; k5 is an integer of 0 to 5, wherein in a case in which k5 is 1, $R^{a8}$ represents a halogen atom, a hydroxy group, a nitro group, or a monovalent organic group having 1 to 20 carbon atoms, and in a case in which k5 is 2 to 5, a plurality of $R^{a8}$s are identical or different from each other, and each $R^{a8}$ represents a halogen atom, a hydroxy group, a nitro group, or a monovalent organic group having 1 to 20 carbon atoms, or the plurality of $R^{a8}$s taken together represent a ring structure having 4 to 20 ring atoms together with the carbon chain to which the plurality of $R^{a8}$s bond.

$R^{a7}$ and $R^{a8}$ each independently represent preferably —$OSO_2$—$R^k$, —$SO_2$—$R^k$, —$OR^k$, —$COOR^k$, —O—CO—$R^k$, —O—$R^{kk}$—$COOR^k$, —$R^{kk}$—CO—$R^{fc}$, —S—$R^k$, a substituted or unsubstituted monovalent hydrocarbon group having 1 to 20 carbon atoms, or a ring structure constituted from at least two selected from these groups taken together, wherein $R^k$ represents a monovalent hydrocarbon group having 1 to 10 carbon atoms; and $R^{kk}$ represents a single bond or a divalent hydrocarbon group having 1 to 10 carbon atoms.

Examples of the monovalent hydrocarbon group having 1 to 20 carbon atoms which may be represented by $R^{a3}$, $R^{a4}$, $R^{a5}$, $R^{a7}$, or $R^{a8}$ include:

linear alkyl groups such as a methyl group, an ethyl group, a n-propyl group, and an n-butyl group;
branched alkyl groups such as an i-propyl group, an i-butyl group, a sec-butyl group, and a t-butyl group;
aryl groups such as a phenyl group, a tolyl group, a xylyl group, a mesityl group, and a naphthyl group;
aralkyl groups such as a benzyl group and a phenethyl group; and the like.

Examples of the divalent organic group which may be represented by $R^{a6}$ include groups obtained by removing one hydrogen atom from the monovalent organic groups having 1 to 20 carbon atoms exemplified as $R^R$ in the above formula (P), and the like.

Examples of the substituent which may substitute for the hydrogen atom included in the hydrocarbon group which may be represented by $R^{a3}$, $R^{a4}$, $R^{a5}$, $R^{a7}$, or $R^{a8}$ include: a halogen atom such as a fluorine atom, a chlorine atom, a bromine atom, or an iodine atom; a hydroxy group; a carboxy group; a cyano group; a nitro group; an alkoxy group; an alkoxycarbonyl group; an alkoxycarbonyloxy group; an acyl group; an acyloxy group; and the like. Of these, the halogen atom is preferred, and a fluorine atom is more preferred.

$R^{a3}$, $R^{a4}$, $R^{a5}$, $R^{a7}$, and $R^{a8}$ each independently represent preferably —$OSO_2$—$R^k$, —$SO_2$—$R^k$, —$OR^k$, an unsubstituted linear or branched monovalent alkyl group, a monovalent fluorinated alkyl group, or an unsubstituted monovalent aromatic hydrocarbon group, more preferably a fluorinated alkyl group, an unsubstituted monovalent aromatic hydrocarbon group, or an alkoxy group, and still more preferably a fluorinated alkyl group or an alkoxy group.

In the formula (T-1), k1 is preferably 0 to 2, more preferably 0 or 1, and still more preferably 0; and t1 is preferably 0 or 1, and more preferably 0. In the formula (T-2), k2 is preferably 0 to 2, more preferably 0 or 1, and still more preferably 1; k3 is preferably 0 to 2, more preferably 0 or 1, and still more preferably 0; r is preferably 2 or 3, and more preferably 2; and t2 is preferably 0 or 1, and more preferably 1. In the formula (T-3), k4 and k5 are each preferably 0 to 2, more preferably 0 or 1, and still more preferably 0.

T+ represents preferably the cation (T-1) or the cation (T-2), more preferably the cation (Z-1), and still more preferably a triphenylsulfonium cation.

Examples of the acid generating agent (B) include: compounds (hereinafter, may be also referred to as "compounds (4-1-1) to (4-1-19)") represented by the following formulae (4-1-1) to (4-1-19) as an acid generating agent which generates sulfonic acid; compounds (hereinafter, may be also referred to as "compounds (4-2-1) to (4-2-3)") represented by the following formulae (4-2-1) to (4-2-3) as an acid generating agent which generates imidic acid; and the like.

(4-1-1)
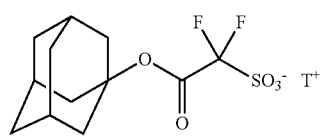

(4-1-2)
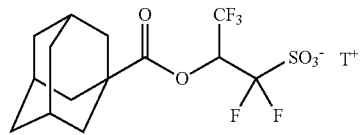

(4-1-3)
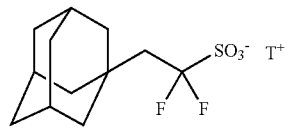

(4-1-4)
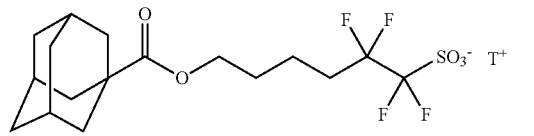

(4-1-5)
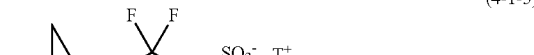

(4-1-6)
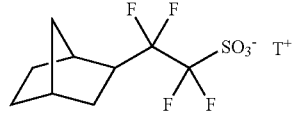

(4-1-7)
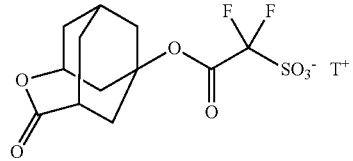

(4-1-8)
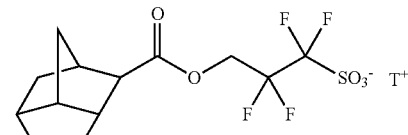

(4-1-9)
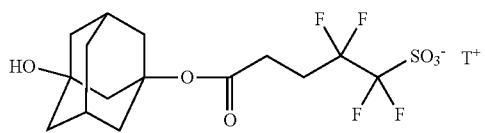

(4-1-10)
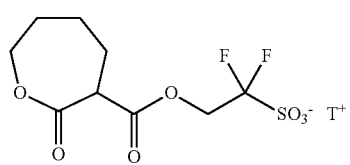

(4-1-11)
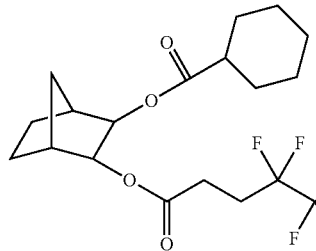

(4-1-12)
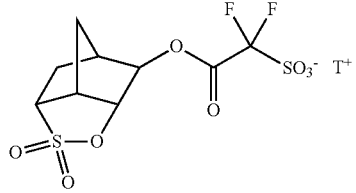

(4-1-13)
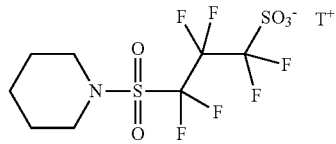

(4-1-14)
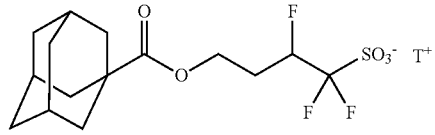

(4-1-15)
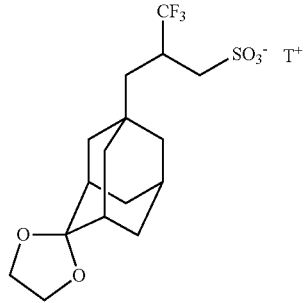

-continued (4-1-16)
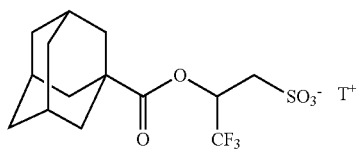

(4-1-17)
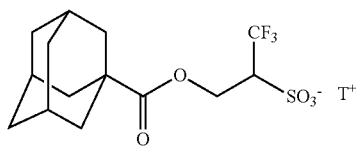

(4-1-18)
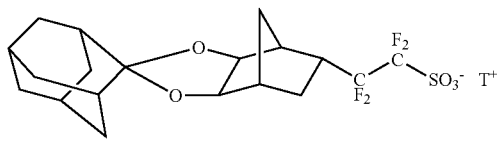

(4-1-19)
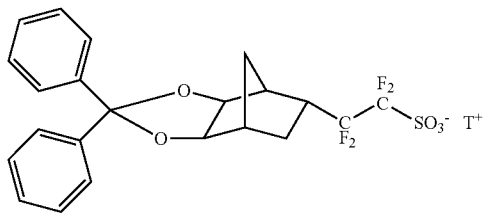

(4-2-1)
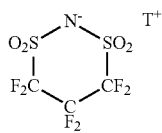

(4-2-2)
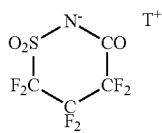

(4-2-3)
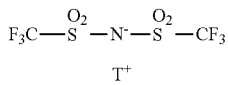

In each of the above formulae (4-1-1) to (4-1-19) and (4-2-1) to (4-2-3), T$^+$ represents a monovalent radiation-sensitive onium cation.

The acid generating agent (B) is preferably the compound (4-1), and more preferably the compound (4-1-1), (4-1-3), (4-1-4), (4-1-16), (4-1-17), or (4-1-19).

In the case in which the acid generator (B) is the acid generating agent (B), the lower limit of a content of the acid generating agent (B) with respect to 100 parts by mass of the polymer (A) is preferably 0.1 parts by mass, more preferably 1 part by mass, and still more preferably 10 parts by mass. The upper limit of the content is preferably 50 parts by mass, more preferably 40 parts by mass, still more preferably 30 parts by mass, and particularly preferably 25 parts by mass. When the content of the acid generating agent (B) falls within the above range, the sensitivity and the process window can be further improved. One, or two or more types of the acid generator (B) may be contained.

(C) Compound

The compound (C) is represented by the following formula (1). In the radiation-sensitive resin composition, the compound (C) acts as an acid diffusion control agent.

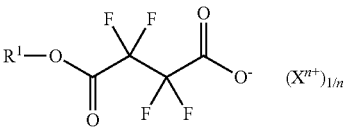

(1)

In the above formula (1). R$^1$ represents a hydrogen atom or a monovalent organic group having 1 to 30 carbon atoms, and X$^{n+}$ represents a radiation-sensitive onium cation having a valency of n, wherein n is an integer of 1 to 3.

Examples of the monovalent organic group having 1 to 30 carbon atoms which may be represented by R$^1$ include groups similar to the groups exemplified as the monovalent organic group having 1 to 20 carbon atoms which may be represented by R$^R$ in the above formula. (P), and the like.

Specific examples of the monovalent organic group having 1 to 30 carbon atoms which may be represented by R$^1$ include:
chain or alicyclic hydrocarbon groups having a tertiary carbon atom as a binding site (more specifically, chain or alicyclic hydrocarbon groups in which a tertiary carbon atom bonds to the oxy-oxygen atom of the carbonyloxy group), such as a t-butyl group, a 1-methylcyclopentan-1-yl group, a 1-ethylcyclopentan-1-yl group, a 1-phenylcyclohexan-1-yl group, a 2-ethyladamantan-2-yl group, and an adamantan-1-yl group;
chain or alicyclic hydrocarbon groups having a secondary carbon atom as a binding site (more specifically, chain or alicyclic hydrocarbon groups in which a secondary carbon atom bonds to the oxy-oxygen atom of the carbonyloxy group), such as a cyclohexyl group, a norbornyl group, and an i-propyl group;
chain hydrocarbon groups having a primary carbon atom as a binding site (more specifically, chain hydrocarbon groups in which a primary carbon atom bonds to the oxy-oxygen atom of the carbonyloxy group), such as an ethyl group and a pentyl group; aromatic hydrocarbon groups such as a phenyl group, a naphthyl group, and a benzyl group;
fluorinated hydrocarbon groups such as a 1,1,1,3,3,3-hexafluoropropan-2-yl group, a 2,2,2-trifluoroethan-1-yl group, a perfluorocyclohexan-1-yl group, and a 2,4,6-trifluorophenyl group; and the like.

The organic group which may be represented by R$^1$ preferably includes a ring structure. When R$^1$ includes the ring structure, diffusion in the resist film of the compound (C) can be more appropriately controlled, and as a result, the process window can be further expanded. The organic group including the ring structure is exemplified by a substituted or unsubstituted alicyclic hydrocarbon group, a substituted or unsubstituted aromatic hydrocarbon group, and the like.

Furthermore, the organic group which may be represented by R$^1$ is preferably an acid-labile group. When R$^1$ represents an acid-labile group, R$^1$ is dissociated by an action of the acid generated from the acid generator (B) or the like upon exposure, thereby generating a carboxy group and improving solubility in the developer solution, and as a result, the process window can be further expanded. Examples of the organic group being the acid-labile group include: the groups exemplified as the chain or alicyclic hydrocarbon groups having the tertian/carbon atom as the binding site, described above (wherein the adamantan-1-yl group is not included); cycloalken-3-yl groups such as a cyclohexen-3-yl group; and the like.

The radiation-sensitive onium cation having a valency of n represented by $X^{n+}$ is exemplified by a sulfonium cation, a tetrahydrothiophenium cation, an iodonium cation, and the like. Of these, the sulfonium cation or the iodonium cation is preferred.

Examples of the sulfonium cation in the case in which n is 1 include the cation (T-1) in the acid generator (B), and the like. Examples of the iodonium cation in the case in which n is 1 include the cation (T-3) in the acid generator (B), and the like.

$X^{n+}$ represents preferably a monovalent sulfonium cation, more preferably the cation (T-1), and still more preferably a triphenylsulfonium cation.

n is preferably 1 or 2, and more preferably 1.

Examples of the compound (C) include compounds (hereinafter, may be also referred to as "compounds (1-1) to (1-9)") represented by the following formulae (1-1) to (1-9), and the like.

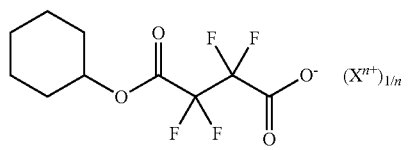 (1-1)

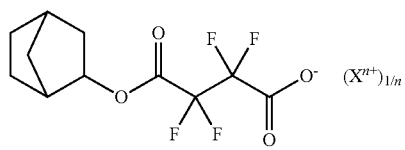 (1-2)

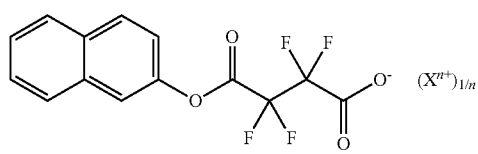 (1-3)

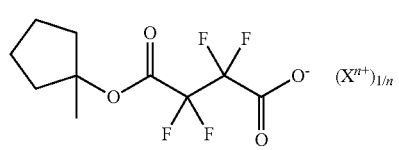 (1-4)

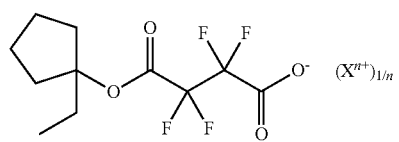 (1-5)

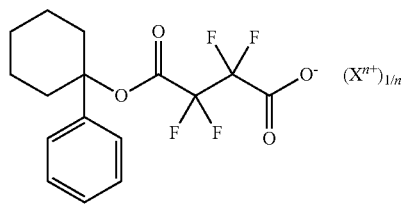 (1-6)

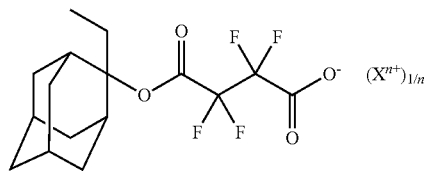 (1-7)

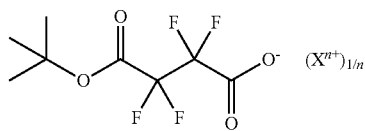 (1-8)

(1-9)

In the above formulae (1-1) to (1-9), $(X^{n+})_{1/n}$ is as defined in the above formula (1).

The lower limit of a content of the compound (C) with respect to 100 parts by mass of the polymer (A) is preferably 0.1 parts by mass, more preferably 0.5 parts by mass, still more preferably 1 part by mass, and particularly preferably 2 parts by mass. The upper limit of the content is preferably 20 parts by mass, more preferably 15 parts by mass, still more preferably 10 parts by mass, and particularly preferably 7 parts by mass.

The lower limit of a content of the compound (C) with respect to 100 mol % of the acid generating agent (B) is preferably 1 mol %, more preferably 5 mol %, still more preferably 10 mol %, and particularly preferably 15 mol %. The upper limit of the content is preferably 100 mol %, more preferably 50 mol %, still more preferably 30 mol %, and particularly preferably 25 mol %.

When the content of the compound (C) falls within the above ranges, the sensitivity and the process window can be further improved.

Method of Synthesizing Compound (C)

The compound (C) can be synthesized, for example, by: allowing a reaction between tetrafluorosuccinic anhydride and an alcohol represented by $R^1$—OH, in a solvent such as dichloromethane in the presence of a base such as triethylamine or the like: and then adding to the reaction product, a salt such as triphenylsulfonium chloride or the like, to conduct an ion exchange.

(D) Solvent

The solvent (D) is not particularly limited as long as it is a solvent capable of dissolving or dispersing at least the polymer (A), the acid generator (B), and the compound (C), and optional components) which is/are contained as desired.

The solvent (D) is exemplified by an alcohol solvent, an ether solvent, a ketone solvent, an amide solvent, an ester solvent, a hydrocarbon solvent, and the like.

Examples of the alcohol solvent include:
aliphatic monohydric alcohol solvents having 1 to 18 carbon atoms such as 4-methyl-2-pentanol and n-hexanol;
alicyclic monohydric alcohol solvents having 3 to 18 carbon atoms such as cyclohexanol;
polyhydric alcohol solvents having 2 to 18 carbon atoms such as 1,2-propylene glycol;

polyhydric alcohol partial ether solvents having 3 to 19 carbon atoms such as propylene glycol-1-monomethyl ether; and the like.

Examples of the ether solvent include:
dialkyl ether solvents such as diethyl ether, dipropyl ether, dibutyl ether, dipentyl ether, diisoamyl ether, dihexyl ether, and diheptyl ether;
cyclic ether solvents such as tetrahydrofuran and tetrahydropyran;
aromatic ring-containing ether solvents such as diphenyl ether and anisole; and the like.

Examples of the ketone solvent include:
chain ketone solvents such as acetone, methyl ethyl ketone, methyl n-propyl ketone, methyl n-butyl ketone, diethyl ketone, methyl iso-butyl ketone, 2-heptanone, ethyl n-butyl ketone, methyl n-hexyl ketone, di-iso-butyl ketone, and trimethylnonanone;
cyclic ketone solvents such as cyclopentanone, cyclohexanone, cycloheptanone, cyclooctanone, and methylcyclohexanone;
2,4-pentanedione, acetonylacetone, and acetophenone; and the like.

Examples of the amide solvent include:
cyclic amide solvents such as N,N'-dimethylimidazolidinone and N-methylpyrrolidone;
chain amide solvents such as N-methylformamide, N,N-dimethylformamide, N,N-diethylformamide, acetamide, N-methyl acetamide, N,N-dimethylacetamide, and N-methylpropionamide; and the like.

Examples of the ester solvent include:
monocarboxylic acid ester solvents such as n-butyl acetate and ethyl lactate:
polyhydric alcohol carboxylate solvents such as propylene glycol acetate;
polyhydric alcohol partial ether carboxylate solvents such as propylene glycol monomethyl ether acetate;
polyhydric carboxylic acid diester solvents such as diethyl oxalate;
carbonate solvents such as dimethyl carbonate and diethyl carbonate; and the like.

Examples of the hydrocarbon solvent include:
aliphatic hydrocarbon solvents having 5 to 12 carbon atoms such as n-heptane and n-hexane;
aromatic hydrocarbon solvents having 6 to 16 carbon atoms such as toluene and xylene; and the like.

Of these, the solvent (D) is preferably the alcohol solvent and/or the ester sol vent, more preferably the polyhydric alcohol partial ether solvent and/or the polyhydric alcohol partial ether carboxylate solvent, and still more preferably propylene glycol-1-monomethyl ether and/or propylene glycol monomethyl ether acetate. One, or two or more types of the solvent (D) may be contained.

Other Optional Component(s)

The other optional component(s) is/are exemplified by an acid diffusion controller (except for those corresponding to the compound (C)), a surfactant, and the like. This/these other optional component(s) may be used alone, or in a combination of two or more.

Acid Diffusion Controller

The acid diffusion controller is able to control a diffusion phenomenon, in the resist film, of the acid generated from the acid generating agent (B) and/or the like upon exposure, thereby serving to inhibit unwanted chemical reaction(s) in a non-exposed region. The acid diffusion controller may be contained in the radiation-sensitive resin composition in the form of a free compound (hereinafter, appropriately referred to as "acid diffusion control agent") or in the form of an acid generator incorporated as a part of the polymer (A) or the like, or may be in a combination of both these forms.

The acid diffusion control agent is exemplified by a nitrogen atom-containing compound, a photodegradable base (except for those corresponding to the compound (C)), and the like. The photodegradable base is a compound that is degraded upon exposure to have lowered basicity.

Examples of the nitrogen-containing compound include: a compound having one nitrogen atom such as monoalkylamine; a compound having two nitrogen atoms such as ethylene diamine; a compound having three or more nitrogen atoms such as polyethylene imine; an amide group-containing compound such as N,N-dimethylacetamide; a urea compound such as 1,1,3,3-tetramethylurea; a nitrogen-containing heterocyclic compound such as N-(undecylcarbonyloxyethyl)morpholine or N-t-butoxycarbonyl-4-hydroxypiperidine; and the like.

Examples of the photodegradable base include triphenyl sulfonium salicylate, triphenylsulfonium 10-camphorsulfonate, triphenylsulfonium adamantan-1-yl oxalate, triphenyl sulfonium 2,3,4,5-tetrafluoro-6-hydroxybenzoate, triphenylsulfonium 5,6-di(cyclohexyloxycarbonyl)norbornane-2-sulfonate, triphenylsulfonium 1,2-di(norbornane-2, 6-lacton-5-yloxycarbonyl)ethane-1-sulfonate, triphenylsulfonium 3-(adamantan-1-yl)-3-hydroxy-2,2-difluoropropionate, triphenylsulfonium 4-cyclohexyloxycarbonyl-2,2,3,3,4,4-hexafluorobutyrate, and the like.

In the case in which the radiation-sensitive resin composition contains the acid diffusion control agent, the lower limit of a content of the acid diffusion control agent with respect to 100 parts by mass of the polymer (A) is preferably 0.1 parts by mass, more preferably 1 part by mass, and still more preferably 2 parts by mass. The upper limit of the content is preferably 20 parts by mass, more preferably 10 parts by mass, and still more preferably 7 parts by mass.

In the case in which the radiation-sensitive resin composition contains the acid diffusion control agent, the lower limit of a content of the acid diffusion control agent with respect to 100 mol % of the acid generating agent (B) is preferably 1 mol %, more preferably 5 mol %, still more preferably 10 mol %, and particularly preferably 15 mol %. The upper limit of the content is preferably 100 mol %, more preferably 50 mol %, still more preferably 30 mol %, and particularly preferably 25 mol %. The radiation-sensitive resin composition may contain one, or two or more types of the acid diffusion controller.

Surfactant

The surfactant exhibits an effect of improving coating properties, striation, developability, and the like. Examples of the surfactant include nonionic surfactants such as polyoxyethylene lauryl ether, and the like. In the case in which the radiation-sensitive resin composition contains the surfactant, the upper limit of a content of the surfactant with respect to 100 parts by mass of the polymer (A) is preferably 2 parts by mass.

Preparation Procedure of Radiation-Sensitive Resin Composition

The radiation-sensitive composition may be prepared by, for example: mixing the polymer (A), the acid generator (B), the compound (C), and the solvent (D), and the other optional component(s), which is/are added as needed, in a predetermined ratio, and preferably filtering a thus resulting mixture through a filter having a pore size of about 0.2 μm, for example.

Method of Forming Resist Pattern

The method of forming a resist pattern of the other embodiment of the present invention includes: a step of applying a radiation-sensitive resin composition directly or indirectly on a substrate (hereinafter, may be also referred to as "applying step"); a step of exposing the resist film formed by the applying step (hereinafter, may be also referred to as "exposing step"); and a step of developing the resist fil m exposed (hereinafter, may be also referred to as "developing step"). In the method of forming a resist pattern, the radiation-sensitive resin composition of the one embodiment of the present invention, described above, is used as the radiation-sensitive resin composition.

According to the method of forming a resist pattern of the other embodiment of the present invention, due to using the radiation-sensitive resin composition of the one embodiment of the present invention, formation of a resist pattern is enabled with superior sensitivity and a broad process window.

Hereinafter, each step will be described.

Applying Step

In this step, the radiation-sensitive resin composition of the one embodiment of the invention is applied directly or indirectly on the substrate. Accordingly, a resist film is formed. The substrate on which the resist film is to be formed is exemplified by a conventionally well-known substrate such as a silicon wafer, a wafer coated with silicon dioxide or aluminum, and the like. Furthermore, the case of indirectly applying the radiation-sensitive resin composition on the substrate is exemplified by applying the radiation-sensitive resin composition on an underlayer film such as an antireflective film formed on the substrate, and the like. Examples of such an antireflective film include an organic or inorganic antireflective film disclosed in Japanese Examined Patent Application, Publication No. H6-12452, Japanese Unexamined Patent Application, Publication No. S59-93448, and the like. An application procedure is exemplified by spin coating, cast coating, roll coating, and the like. After the application, prebaking (PB) may be carried out as needed for evaporating the solvent remaining in the coating film. The lower limit of a PB temperature is preferably 60° C., and more preferably 80° C. The upper limit of the PB temperature is preferably 160° C., and more preferably 140° C. The lower limit of a PB time period is preferably 5 sec, and more preferably 10 sec. The upper limit of the PB time period is preferably 600 sec, and more preferably 300 sec. The lower limit of an average thickness of the resist film formed is preferably 10 nm, and more preferably 20 nm. The upper limit of the average thickness is preferably 1,000 nm, and more preferably 500 nm. It is to be noted that the average thickness of the film is a value measured using a spectroscopic ellipsometer ("M200D," available from J.A. Woollam Co.).

Exposing Step

In this step, the resist film formed by the applying step is exposed. This exposure is carried out by irradiation with an exposure light through a photomask (as the case may be, through a liquid immersion medium such as water). Examples of the exposure light include electromagnetic waves such as visible light rays, ultraviolet rays, far ultraviolet rays, extreme ultraviolet rays (EUV), X-rays, and γ-rays; charged particle rays such as electron beams and α-rays; and the like, which may be selected in accordance with a line width of the intended pattern. Of these, far ultraviolet rays, EUV, or an electron beam is preferred; an ArF excimer laser beam (wavelength: 193 nm), a KrF excimer laser beam (wavelength: 248 nm), EUV, or an electron beam is more preferred; and EUV or an electron beam is still more preferred.

It is preferred that post exposure baking (PEB) is carried out after the exposure to promote dissociation of the acid-labile group included in the polymer (A), etc. mediated by the acid generated from the acid generator (B), etc. upon the exposure in exposed regions of the resist film. This PEB enables an increase in a difference in solubility of the resist film in the developer solution between the light-exposed regions and light-unexposed regions. The lower limit of a PEB temperature is preferably 50° C., and more preferably 80° C. The upper limit of the PEB temperature is preferably 180° C., and more preferably 140° C. The lower limit of a PEB time period is preferably 5 sec, and more preferably 10 sec. The upper limit of the PEB time period is preferably 600 sec, and more preferably 300 sec.

Developing Step

In this step, the resist film exposed is developed. Accordingly, formation of a predetermined resist pattern is enabled. After the development, washing with a rinse agent such as water or an alcohol, followed by drying is typically carried out. The development procedure in the developing step may be carried out by either development with an alkali, or development with an organic solvent. Of these, the development with an alkali is preferred.

In the case of the development with an alkali, an alkali developer solution for use in the development is exemplified by alkaline aqueous solutions prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyl di ethylamine, ethyl dim ethyl amine, triethanolamine, tetramethyl ammonium hydroxide (TMAH), pyrrole, piperidine, choline, 1,8-diazabicyclo-[5.4.0]-7-undecene, 1,5-diazabi-cyclo-[4.3.0]-5-nonene, etc., and the like. Of these, an aqueous TMAH solution is preferred, and a 2.38% by mass aqueous TMAH solution is more preferred.

In the case of the development with an organic solvent, the developer solution is exemplified by: an organic solvent such as a hydrocarbon solvent, an ether solvent, an ester solvent, a ketone solvent and an alcohol solvent; a solvent containing the organic solvent; and the like. An exemplary organic solvent includes one, or two or more types of the solvents exemplified as the solvent (D) in the radiation-sensitive resin composition, described above, and the like. Of these, the ester solvent or the ketone solvent is preferred. The ester solvent is preferably an acetic acid ester solvent, and more preferably n-butyl acetate. The ketone solvent is preferably the chain ketone, and more preferably 2-heptanone. The lower limit of the content of the organic solvent in the developer solution is preferably 80% by mass, more preferably 90% by mass, still more preferably 95% by mass, and particularly preferably 99% by mass. Components other than the organic solvent in the organic solvent developer solution are exemplified by water, silicone oil, and the like.

Examples of the development procedure include: a dipping procedure in which the substrate is immersed for a given time period in the developer solution charged in a container; a puddle procedure in which the developer solution is placed to form a dome-shaped bead by way of the surface tension on the surface of the substrate for a given time period to conduct a development; a spraying procedure in which the developer solution is sprayed onto the surface of the substrate; a dynamic dispensing procedure in which the developer solution is continuously applied onto the substrate, which is rotated at a constant speed, while scanning with a developer solution-application nozzle at a constant speed; and the like.

Compound

The compound according to the still another embodiment of the present invention is represented by the following formula (1). The compound can be favorably used as an acid diffusion control agent in a radiation-sensitive resin composition.

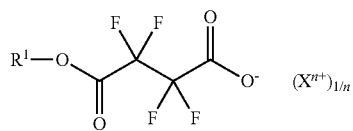

(1)

In the above formula (1), $R^1$ represents a hydrogen atom or a monovalent organic group having 1 to 30 carbon atoms; and $X^{n+}$ represents a cation having a valency of n, wherein n is an integer of 1 to 3.

Examples of the cation having a valency of n represented by $X^{n+}$ include:
- a monovalent onium cation, an alkali metal cation, or the like as a monovalent cation;
- a divalent onium cation, an alkaline earth metal cation, or the like as a divalent cation;
- a trivalent onium cation, a trivalent metal cation, or the like as a trivalent cation; and the like.

The onium cation may be either radiation sensitive, or radiation insensitive. Examples of the radiation-sensitive onium cation include such cations as those exemplified as the radiation-sensitive onium cation represented by $T^+$ in the formula (4) for the acid generating agent (B), described above, i.e., a sulfonium cation, an iodonium cation, a tetrahydrothiophenium cation, and the like. The divalent or trivalent cation may be exemplified by both a cation having a cation moiety of either +2 or +3 charge, and a cation that includes two or three cation moieties each having +1 charge.

The cation represented by $X^{n+}$ in the above formula (1) is preferably an onium cation. This onium cation is preferably radiation sensitive.

EXAMPLES

Hereinafter, the present invention is explained in detail by way of Examples, but the present invention is not in any way limited to these Examples. Physical property values in the Examples were measured as described below.

Weight Average Molecular Weight (Mw), Number Average Molecular Weight (Mn) and Dispersity Index (Mw/Mn)

Measurements were carried out by gel permeation chromatography (GPC) using GPC columns produced by Tosoh Corporation ("G2000 HXL"×2, "G3000 HXL"×1, and "G4000 HXL"×1) under an analytical conditions involving a flow rate of 1.0 mL/min, an elution solvent of tetrahydrofuran, a sample concentration of 1.0% by mass, an injected sample amount of 100 μL a column temperature of 40° C., and a differential refractometer as a detector, with monodispersed polystyrene as a standard. Furthermore, a dispersity index (Mw/Mn) was calculated according to measurement results of the Mw and the Mn.

Proportion of Each Structural Unit of Polymer

The proportion of each structural unit of each polymer was determined by $^{13}$C-NMR analysis using a nuclear magnetic resonance apparatus ("JNM-Delta400," available from JEOL, Ltd.).

Synthesis of Polymer (A)

Monomers used for synthesizing the polymer (A) are shown below. It is to be noted that in the following Synthesis Examples, unless otherwise specified particularly, the term "parts by mass" means a value, provided that the total mass of the monomers used was 100 parts by mass, and the term "mol %" means a value, provided that the total mol number of the monomers used was 100 mol %.

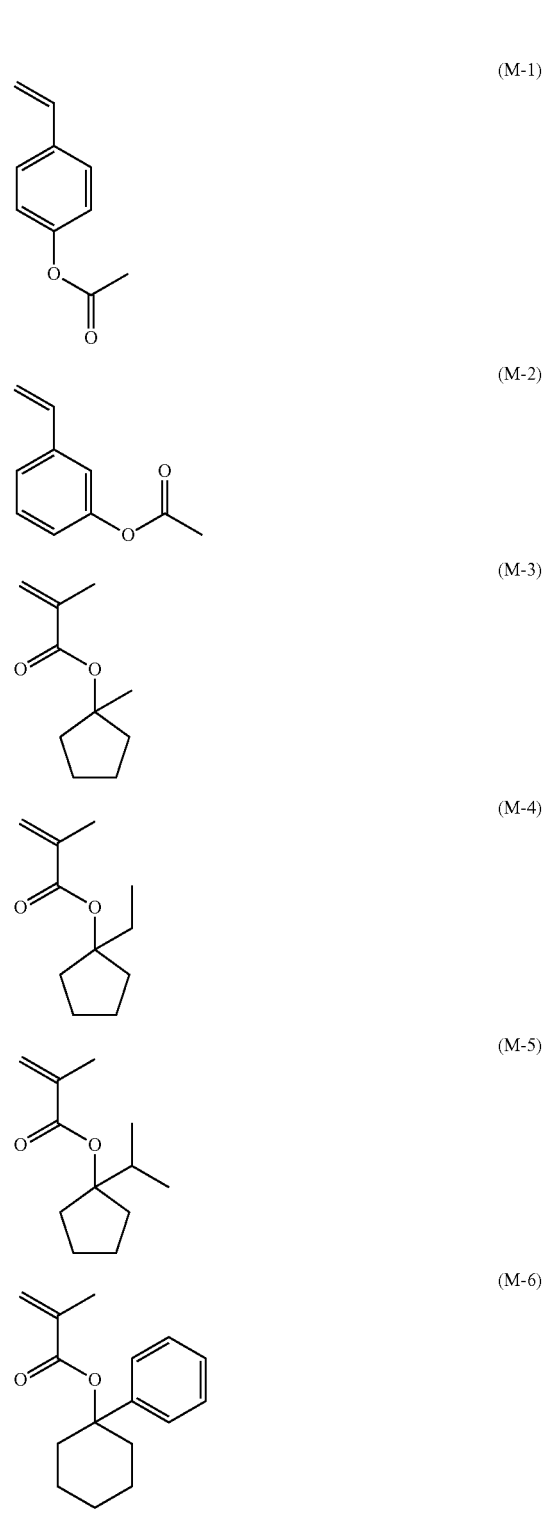

-continued (M-7)
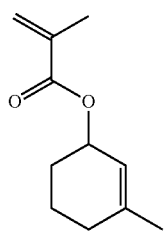

(M-8)
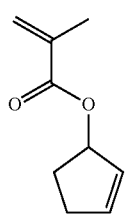

(M-9)
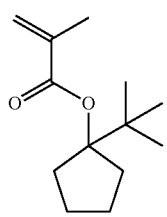

(M-10)
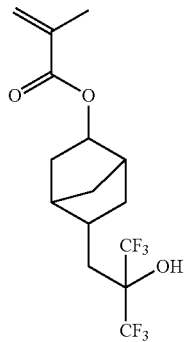

(M-11)
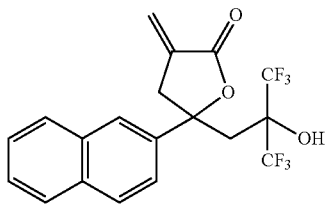

Synthesis Example 1: Synthesis of Polymer (A-1)

The monomer (M-3) and the monomer (M-1) were dissolved in 200 parts by mass of propylene glycol-1-monomethyl ether such that the molar ratio became 60/40. Next, a monomer solution was prepared by adding 6 mol % azobisisobutyronitrile (AIBN) as a radical polymerization initiator. Meanwhile, to an empty reaction vessel were charged 100 parts by mass of propylene glycol-1-monomethyl ether, which were then heated to 85° C. with stirring. Next, the monomer solution prepared as described above was added dropwise to the reaction vessel over 3 hrs, and then a thus resulting solution was further heated for 3 hrs at 85° C., and a polymerization reaction was allowed to proceed for 6 hrs. After completion of the polymerization reaction, the polymerization solution was cooled to room temperature.

The polymerization solution thus cooled was charged into 500 parts by mass of hexane with respect to 100 parts by mass of the polymerization solution, and a thus precipitated white powder was filtered off. The white powder obtained by the filtration was washed twice with 100 parts by mass of hexane with respect to 100 parts by mass of the polymerization solution, followed by filtering off and dissolution in 300 parts by mass of propylene glycol-1-monomethyl ether. Next, 500 parts by mass of methanol, 50 parts by mass of triethylamine, and 10 parts by mass of ultra-pure water were added to a resulting solution, and a hydrolysis reaction was performed at 70° C. for 6 hrs with stirring.

After completion of the reaction, the remaining solvent was distilled away and a solid thus obtained was dissolved in 100 parts by mass of acetone. A thus obtained solution was added drop wise to 500 parts by mass of water to permit coagulation of the polymer, and a solid thus obtained was filtered off. Drying at 50° C. for 12 hrs gave a white powdery polymer (A-1). The Mw of the polymer (A-1) was 5,700, and the Mw/Mn was 1.61. Furthermore, as a result of the $^{13}$C-NMR analysis, the proportions of the structural units derived from (M-3) and (M-1) were, respectively, 59.1 mol % and 40.9 mol %.

Synthesis Examples 2 to 9

Polymers (A-2) to (A-9) were synthesized by a similar operation to that of Synthesis Example 1 except that each monomer of the type and in the proportion shown in Table 1 below was used. It is to be noted that in Table 1, "-" indicates that the corresponding monomer was not used.

TABLE 1

| | (A) Polymer | Monomer that gives structural unit (I) | | proportion of structural unit (mol %) | Monomer that gives structural unit (II) | | proportion of structural unit (mol %) | Monomer that gives other structural unit | | proportion of structural unit (mol %) | Mw | Mw/Mn |
|---|---|---|---|---|---|---|---|---|---|---|---|---|
| | | type | proportion (mol %) | | Type | proportion (mol %) | | type | proportion (mol %) | | | |
| Synthesis Example 1 | A-1 | M-3 | 60 | 59.1 | M-1 | 40 | 40.9 | — | — | — | 5,700 | 1.61 |
| Synthesis Example 2 | A-2 | M-4 | 60 | 57.2 | M-1 | 40 | 42.8 | — | — | — | 5,800 | 1.64 |
| Synthesis Example 3 | A-3 | M-5 | 60 | 55.8 | M-1/M-2 | 30/10 | 30.2/14.0 | — | — | — | 6,100 | 1.65 |
| Synthesis Example 4 | A-4 | M-6 | 60 | 56.1 | M-1 | 40 | 43.9 | — | — | — | 6,200 | 1.50 |

TABLE 1-continued

| | (A) Polymer | Monomer that gives structural unit (I) | | | Monomer that gives structural unit (II) | | | Monomer that gives other structural unit | | | Mw | Mw/Mn |
|---|---|---|---|---|---|---|---|---|---|---|---|---|
| | | type | proportion (mol %) | proportion of structural unit (mol %) | Type | proportion (mol %) | proportion of structural unit (mol %) | type | proportion (mol %) | proportion of structural unit (mol %) | | |
| Synthesis Example 5 | A-5 | M-7 | 60 | 59.5 | M-1 | 40 | 40.5 | — | — | — | 5,500 | 1.54 |
| Synthesis Example 6 | A-6 | M-8 | 60 | 59.7 | M-1 | 40 | 40.3 | — | — | — | 5,400 | 1.53 |
| Synthesis Example 7 | A-7 | M-9 | 60 | 55.3 | M-1 | 40 | 44.7 | — | — | — | 6,000 | 1.67 |
| Synthesis Example 8 | A-8 | M-3 | 60 | 58.9 | M-1 | 30 | 32.2 | M-10 | 10 | 8.9 | 6,900 | 1.70 |
| Synthesis Example 9 | A-9 | M-3 | 60 | 59.2 | M-1 | 30 | 31.6 | M-11 | 10 | 9.2 | 6,800 | 1.65 |

Synthesis of Compound (C)

Example 1: Synthesis of Compound (Z-1)

Compound (Z-1) was synthesized according to the following reaction scheme.

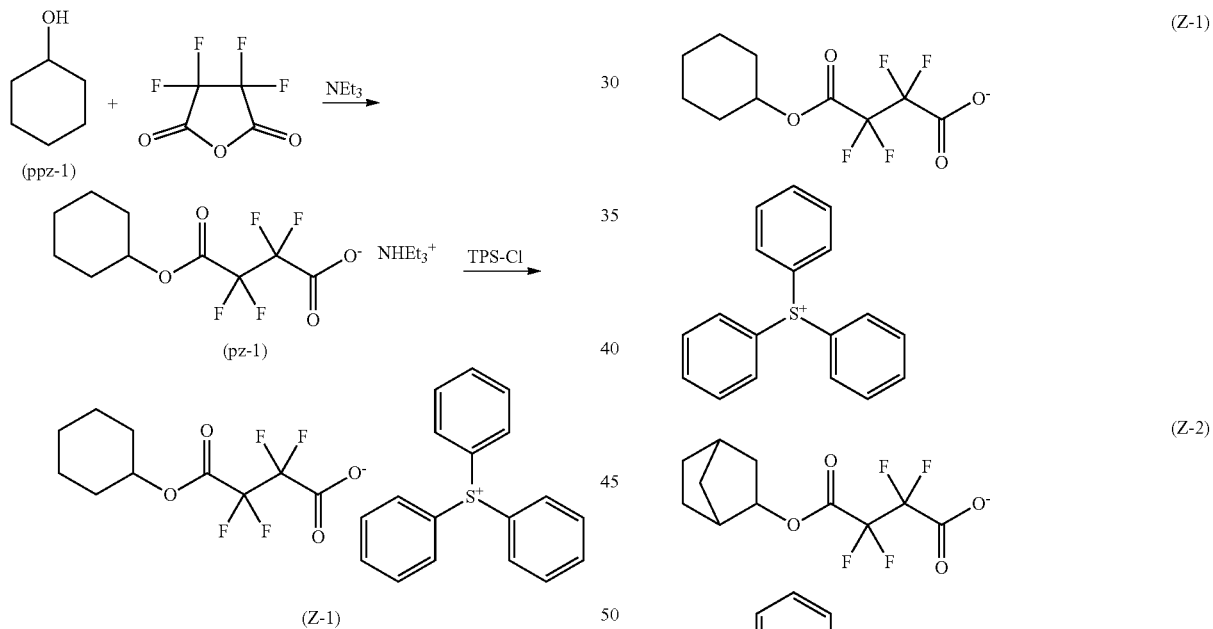

Into a reaction vessel were charged 29 mmol of cyclohexanol as a compound represented by the above formula (ppz-1), 29 mmol of triethylamine (NEt$_3$), and 100 g of dichloromethane. After stirring a resulting mixture at 0° C., 14.5 mmol of tetrafluorosuccinic anhydride was added dropwise. After stirring a resulting mixture for 12 hrs at room temperature, 100 g of water and 16 mmol of triphenylsulfonium chloride (TPS-Cl) were added to a thus generated compound represented by the above formula (pz-1), i.e., triethylammonium 2-(cyclohexylcarbonyl)-1,1,2,2-tetrafluoro-propionate. A resulting mixture was stirred for 2 hrs at room temperature, and then an organic layer was separated, and was thereafter washed with water. After drying over anhydrous sodium sulfate, the solvent was distilled off, and recrystallization gave a compound (Z-1).

Examples 2 to 9: Synthesis of Compounds (Z-2) to (Z-9)

Compounds represented by the following formulae (Z-2) to (Z-9) were synthesized in a similar manner to Example 1 by appropriately selecting precursors.

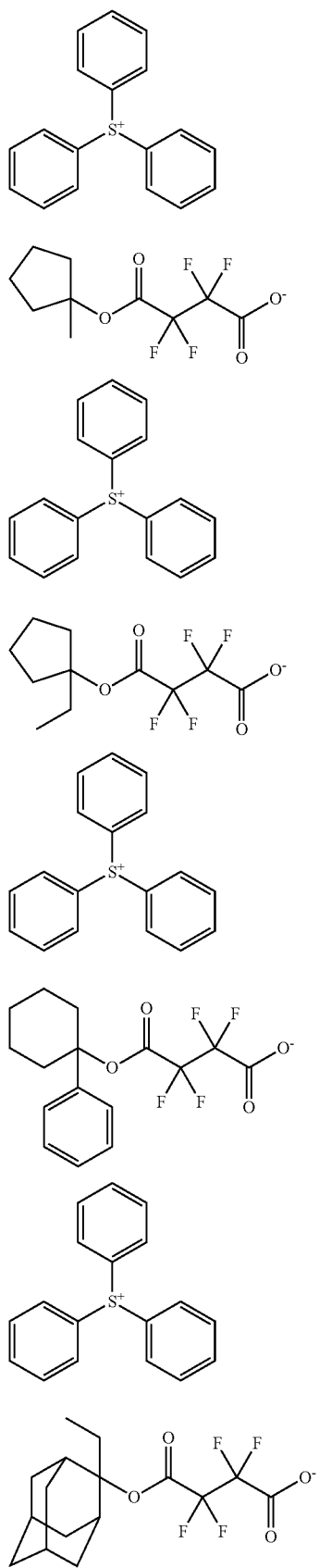

(Z-4)
(Z-5)
(Z-6)
(Z-7)

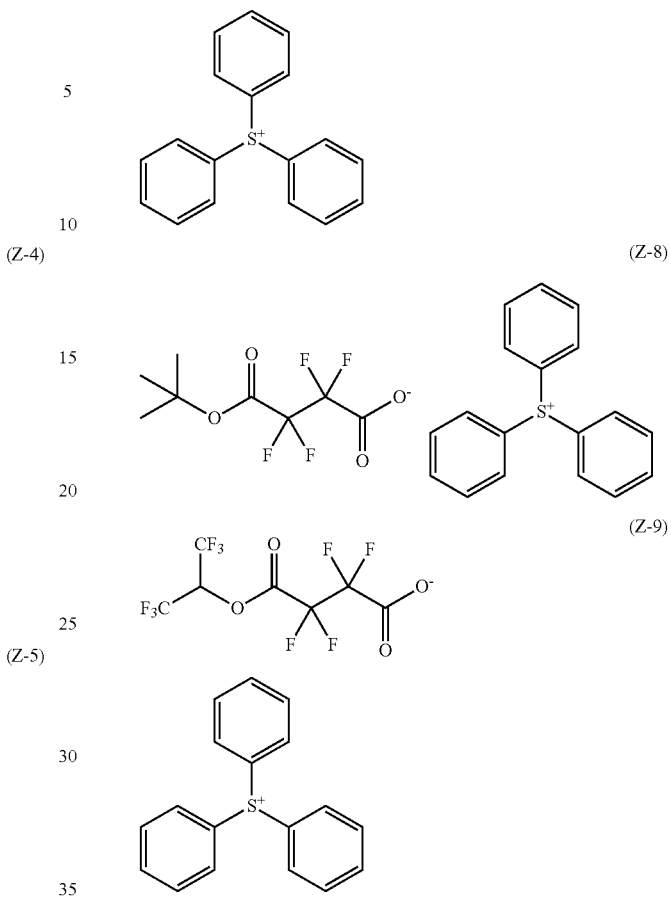

(Z-8)
(Z-9)

Preparation of Radiation-Sensitive Resin Composition

The acid generating agent (B) and the solvent (D) used in preparing each radiation-sensitive resin composition of the one embodiment of the present invention, and the acid diffusion control agent (E) used in preparing each radiation-sensitive resin composition of the Comparative Examples are shown below.

(B) Acid Generating Agent

B-1 to B-6: Compounds represented by the following formulae (B-1) to (B-16)

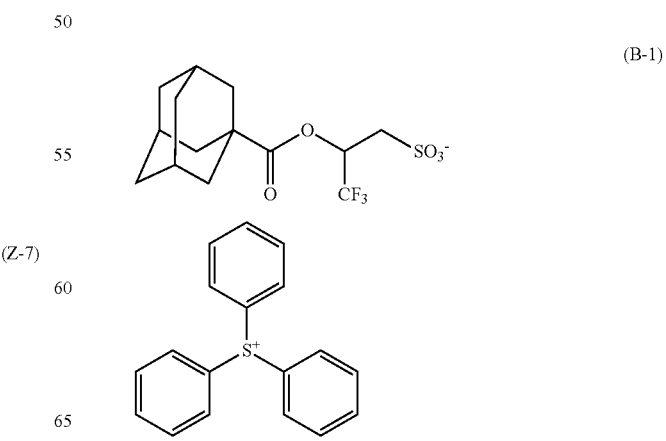

(B-1)

(B-2)
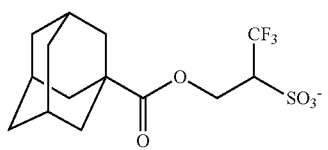

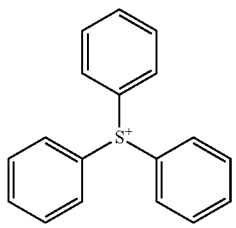

(B-3)
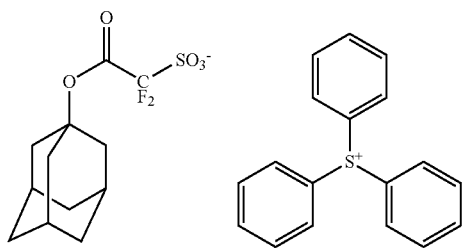

(B-4)
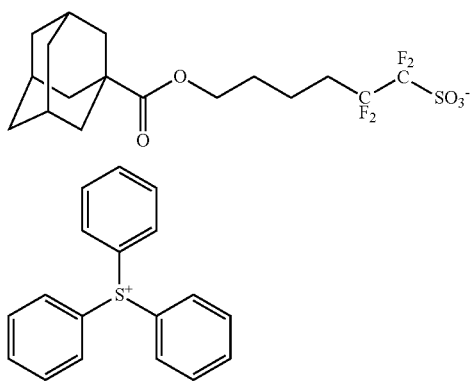

(B-5)
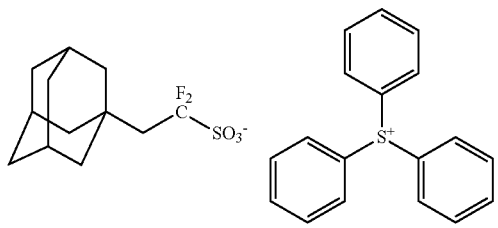

(B-6)
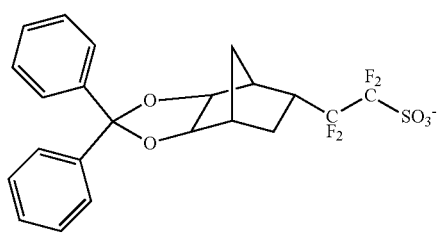

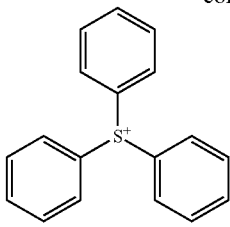

(D) Solvent
D-1: propylene glycol monomethyl ether acetate
D-2: propylene glycol 1-monomethyl ether
(E) Acid Diffusion Control Agent
E-1 to E-3: Compounds represented by the following formulae (E-1) to (E-3)

(E-1)
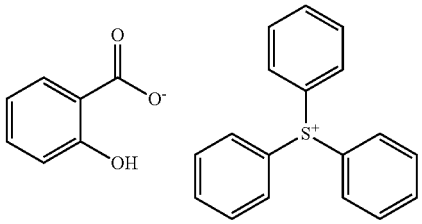

(E-2)
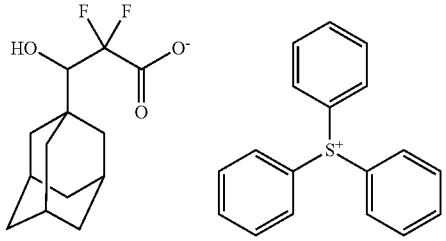

(E-3)
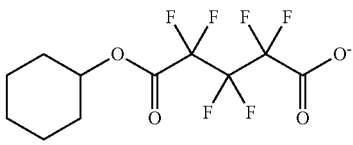

Example 10

A radiation-sensitive resin composition (R-1) was prepared by: blending 100 parts by mass of (A-1) as the polymer (A), 20 parts by mass of (B-1) as the acid generating agent (B), 20 mol % with respect to 100% mol (B-1) of (Z-1) as the acid diffusion control agent (C), and 4,800 parts by mass of (D-1) and 2,000 parts by mass of (D-2) as the organic solvent (D), and then filtering a thus resulting mixture through a membrane filter having a pore size of 0.2 μm.

Examples 11 to 31 and Comparative Examples 1 to 3

Radiation-sensitive resin compositions (R-2) to (R-22) and (CR-1) to (CR-3) were prepared in a similar manner to Example 10, except that for each component, the type and content shown in Table 2 below were used.

TABLE 2

| | Radiation-sensitive resin composition | (A) Polymer type | content (parts by mass) | (B) Acid generating agent type | content (parts by mass) | (C) Compound or (E) Acid diffusion control agent type | content (mol % with respect to 100 mol % of (B)) | (D) Solvent type | content (parts by mass) |
|---|---|---|---|---|---|---|---|---|---|
| Example 10 | R-1 | A-1 | 100 | B-1 | 20 | Z-1 | 20 | D-1/D-2 | 4,800/2,000 |
| Example 11 | R-2 | A-1 | 100 | B-1 | 20 | Z-2 | 20 | D-1/D-2 | 4,800/2,000 |
| Example 12 | R-3 | A-1 | 100 | B-1 | 20 | Z-3 | 20 | D-1/D-2 | 4,800/2,000 |
| Example 13 | R-4 | A-1 | 100 | B-1 | 20 | Z-4 | 20 | D-1/D-2 | 4,800/2,000 |
| Example 14 | R-5 | A-1 | 100 | B-1 | 20 | Z-5 | 20 | D-1/D-2 | 4,800/2,000 |
| Example 15 | R-6 | A-1 | 100 | B-1 | 20 | Z-6 | 20 | D-1/D-2 | 4,800/2,000 |
| Example 16 | R-7 | A-1 | 100 | B-1 | 20 | Z-7 | 20 | D-1/D-2 | 4,800/2,000 |
| Example 17 | R-8 | A-1 | 100 | B-1 | 20 | Z-8 | 20 | D-1/D-2 | 4,800/2,000 |
| Example 18 | R-9 | A-1 | 100 | B-1 | 20 | Z-9 | 20 | D-1/D-2 | 4,800/2,000 |
| Example 19 | R-10 | A-1 | 100 | B-2 | 20 | Z-1 | 20 | D-1/D-2 | 4,800/2,000 |
| Example 20 | R-11 | A-1 | 100 | B-3 | 20 | Z-1 | 20 | D-1/D-2 | 4,800/2,000 |
| Example 21 | R-12 | A-1 | 100 | B-4 | 20 | Z-1 | 20 | D-1/D-2 | 4,800/2,000 |
| Example 22 | R-13 | A-1 | 100 | B-5 | 20 | Z-1 | 20 | D-1/D-2 | 4,800/2,000 |
| Example 23 | R-14 | A-1 | 100 | B-6 | 20 | Z-1 | 20 | D-1/D-2 | 4,800/2,000 |
| Example 24 | R-15 | A-2 | 100 | B-1 | 20 | Z-1 | 20 | D-1/D-2 | 4,800/2,000 |
| Example 25 | R-16 | A-3 | 100 | B-1 | 20 | Z-1 | 20 | D-1/D-2 | 4,800/2,000 |
| Example 26 | R-17 | A-4 | 100 | B-1 | 20 | Z-1 | 20 | D-1/D-2 | 4,800/2,000 |
| Example 27 | R-18 | A-5 | 100 | B-1 | 20 | Z-1 | 20 | D-1/D-2 | 4,800/2,000 |
| Example 28 | R-19 | A-6 | 100 | B-1 | 20 | Z-1 | 20 | D-1/D-2 | 4,800/2,000 |
| Example 29 | R-20 | A-7 | 100 | B-1 | 20 | Z-1 | 20 | D-1/D-2 | 4,800/2,000 |
| Example 30 | R-21 | A-8 | 100 | B-1 | 20 | Z-1 | 20 | D-1/D-2 | 4,800/2,000 |
| Example 31 | R-22 | A-9 | 100 | B-1 | 20 | Z-1 | 20 | D-1/D-2 | 4,800/2,000 |
| Comparative Example 1 | CR-1 | A-1 | 100 | B-1 | 20 | E-1 | 20 | D-1/D-2 | 4,800/2,000 |
| Comparative Example 2 | CR-2 | A-1 | 100 | B-1 | 20 | E-2 | 20 | D-1/D-2 | 4,800/2,000 |
| Comparative Example 3 | CR-3 | A-1 | 100 | B-1 | 20 | E-3 | 20 | D-1/D-2 | 4,800/2,000 |

Resist Pattern Formation

Using a spin coater ("CLEAN TRACK ACT 12," available from Tokyo Electron Limited), the radiation-sensitive resin compositions prepared as described above were each applied on a surface of a 12-inch silicon wafer with an underlayer film ("AL412," available from Brewer Science, Inc.) having an average thickness of 20 nm being formed thereon, and PB was conducted at 130° C. for 60 sec. Thereafter, by cooling at 23° C. for 30 sec, a resist film having an average thickness of 50 nm was formed. Next, the resist film was irradiated with EUV using an EUV scanner ("NXE3300", available from ASML Co., with NA of 0.33 under an illumination condition of Conventional s=0.89, and with a mask of imecDEFECT32FFR02). After the irradiation, PEB was carried out on the resist film at 130° C. for 60 sec. Thereafter, the resist film was developed at 23° C. for 30 sec by using a 2.38% by mass aqueous TMAH solution to form a positive-tone 32 nm line-and-space pattern.

Evaluations

With regard to the resist patterns formed as described above, each radiation-sensitive resin composition was evaluated on the sensitivity and the process window thereof in accordance with the following methods. It is to be noted that a scanning electron microscope ("CG-4100," available from Hitachi High-Technologies Corporation) was used for line-width measurement of the resist patterns. The results of the evaluations are shown in Table 3 below.

Sensitivity

An exposure dose at which a 32-nm line-and-space pattern was formed in the aforementioned resist pattern formation was defined as an optimum exposure dose, and this optimum exposure dose was adopted as sensitivity (mJ/cm$^2$). The sensitivity was evaluated to be: "favorable" in a case of being no greater than 30 mJ/cm$^2$; and "unfavorable" in a case of being greater than 30 mJ/cm$^2$.

Process Window

Using a mask for forming a 32-nm line-and-space pattern (1L/1S), patterns were formed with exposure doses ranging from low to high exposure doses. In general, defects in connections between patterns and the like can be found on the low exposure dose side, and defects such as pattern collapses can be found on the high exposure dose side. The difference between the upper limit value and the lower limit value of resist dimensions at which no such defects were found was considered to be the "CD (Critical Dimension) margin." It is considered that the CD margin (nm) being larger indicates that the process window is broader. The CD margin was evaluated to be: "favorable" in a case of being no less than 30 nm; and "unfavorable" in a case of being less than 30 nm.

TABLE 3

| | Radiation-sensitive resin composition | Sensitivity (mJ/cm$^2$) | CD margin (nm) |
|---|---|---|---|
| Example 10 | R-1 | 27 | 40 |
| Example 11 | R-2 | 26 | 38 |

TABLE 3-continued

| | Radiation-sensitive resin composition | Sensitivity (mJ/cm$^2$) | CD margin (nm) |
|---|---|---|---|
| Example 12 | R-3 | 25 | 39 |
| Example 13 | R-4 | 25 | 41 |
| Example 14 | R-5 | 25 | 43 |
| Example 15 | R-6 | 24 | 45 |
| Example 16 | R-7 | 25 | 44 |
| Example 17 | R-8 | 28 | 36 |
| Example 18 | R-9 | 27 | 37 |
| Example 19 | R-10 | 25 | 41 |
| Example 20 | R-11 | 24 | 43 |
| Example 21 | R-12 | 25 | 42 |
| Example 22 | R-13 | 28 | 44 |
| Example 23 | R-14 | 26 | 47 |
| Example 24 | R-15 | 28 | 43 |
| Example 25 | R-16 | 28 | 42 |
| Example 26 | R-17 | 29 | 44 |
| Example 27 | R-18 | 27 | 41 |
| Example 28 | R-19 | 28 | 42 |
| Example 29 | R-20 | 29 | 39 |
| Example 30 | R-21 | 26 | 42 |
| Example 31 | R-22 | 25 | 44 |
| Comparative Example 1 | CR-1 | 42 | 20 |
| Comparative Example 2 | CR-2 | 33 | 35 |
| Comparative Example 3 | CR-3 | 24 | 17 |

As is clear from the results shown in Table 3, when compared to the Comparative Examples, all of the radiation-sensitive resin compositions of the Examples were favorable in terms of the sensitivity and the CD margin.

The radiation-sensitive resin composition and the method of forming a resist pattern of the embodiments of the present invention enable forming a resist pattern, with superior sensitivity and the broad process window. The compound of the still another embodiment of the present invention can be suitably used as a component of the radiation-sensitive resin composition. Therefore, these can be suitably used in manufacturing processes of semiconductor devices, in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

What is claimed is:

1. A radiation-sensitive resin composition comprising:
a polymer which comprises a structural unit comprising an acid-labile group;
a radiation-sensitive acid generator; and
a compound represented by formula (1):

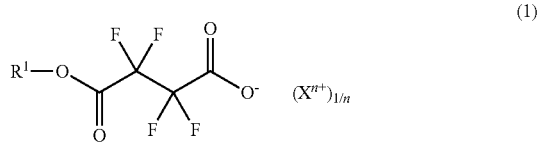

(1)

wherein, in the formula (1), $R^1$ represents a monovalent organic group having 1 to 30 carbon atoms; and $X^{n+}$ represents a radiation-sensitive onium cation having a valency of n, wherein n is an integer of 1 to 3.

2. The radiation-sensitive resin composition according to claim 1, wherein $R^1$ in the formula (1) represents an organic group, and the organic group comprises a ring structure.

3. The radiation-sensitive resin composition according to claim 1, wherein $R^1$ in the formula (1) represents an organic group, and the organic group is an acid-labile group.

4. The radiation-sensitive resin composition according to claim 1, wherein $X^{n+}$ in the formula (1) represents a sulfonium cation, an iodonium cation, or a combination thereof.

5. The radiation-sensitive resin composition according to claim 1, wherein n in the formula (1) is 1.

6. A method of forming a resist pattern, the method comprising:
applying a radiation-sensitive resin composition directly or indirectly on a substrate;
exposing a resist film formed by the applying; and
developing the resist film exposed, wherein
the radiation-sensitive resin composition comprises:
a polymer which comprises a structural unit comprising an acid-labile group;
a radiation-sensitive acid generator; and
a compound represented by formula (1):

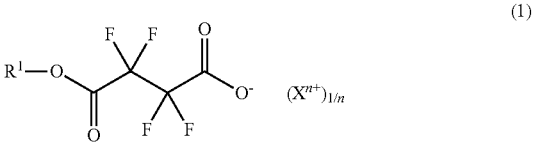

(1)

wherein, in the formula (1), $R^1$ represents a hydrogen atom or a monovalent organic group having 1 to 30 carbon atoms; and $X^{n+}$ represents a radiation-sensitive onium cation having a valency of n, wherein n is an integer of 1 to 3.

7. A compound represented by formula (1):

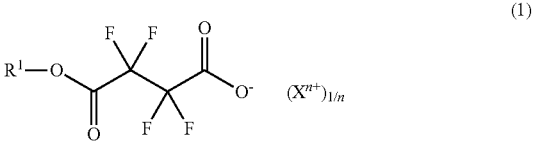

(1)

wherein, in the formula (1), $R^1$ represents a monovalent organic group having 1 to 30 carbon atoms; and $X^{n+}$ represents a cation having a valency of n, wherein n is an integer of 1 to 3.

8. The compound according to claim 7, wherein the cation represented by $X^{n+}$ in the formula (1) is an onium cation.

9. The compound according to claim 8, wherein the onium cation represented by $X^{n+}$ is radiation sensitive.

10. The radiation-sensitive resin composition according to claim 1, wherein the radiation-sensitive acid generator is an acid generating agent, and a content of the acid generating agent in the radiation-sensitive resin composition is from 0.1 parts by mass to 50 parts by mass with respect to 100 parts by mass of the polymer.

11. The radiation-sensitive resin composition according to claim 1, wherein the radiation-sensitive acid generator is an acid generating agent, and a content of the acid generating agent in the radiation-sensitive resin composition is from 10 parts by mass to 40 parts by mass with respect to 100 parts by mass of the polymer.

12. The radiation-sensitive resin composition according to claim 1, wherein the radiation-sensitive acid generator is an acid generating agent, and a content of the compound in the radiation-sensitive resin composition is from 1 to 50 mol % with respect to 100 mol % of the acid generating agent.

13. The radiation-sensitive resin composition according to claim 1, wherein the radiation-sensitive acid generator is an acid generating agent, and a content of the compound in the radiation-sensitive resin composition is from 10 to 30 mol % with respect to 100 mol % of the acid generating agent.

14. The method according to claim 6, wherein the radiation-sensitive acid generator is an acid generating agent, and a content of the acid generating agent in the radiation-sensitive resin composition is from 0.1 parts by mass to 50 parts by mass with respect to 100 parts by mass of the polymer.

15. The method according to claim 6, wherein the radiation-sensitive acid generator is an acid generating agent, and a content of the acid generating agent in the radiation-sensitive resin composition is from 10 parts by mass to 40 parts by mass with respect to 100 parts by mass of the polymer.

16. The method according to claim 6, wherein the radiation-sensitive acid generator is an acid generating agent, and a content of the compound in the radiation-sensitive resin composition is from 1 to 50 mol % with respect to 100 mol % of the acid generating agent.

17. The method according to claim 6, wherein the radiation-sensitive acid generator is an acid generating agent, and a content of the compound in the radiation-sensitive resin composition is from 10 to 30 mol % with respect to 100 mol % of the acid generating agent.

18. The method according to claim 6, wherein $X^{n+}$ in the formula (1) represents a sulfonium cation, an iodonium cation, or a combination thereof.

19. The compound according to claim 9, wherein $X^{n+}$ in the formula (1) represents a sulfonium cation, an iodonium cation, or a combination thereof.

* * * * *